US 11,945,801 B2

(12) United States Patent
Brown et al.

(10) Patent No.: US 11,945,801 B2
(45) Date of Patent: Apr. 2, 2024

(54) BICYCLIC AZA COMPOUNDS AS MUSCARINIC $M_1$ AND/OR $M_4$ RECEPTOR AGONISTS

(71) Applicant: Heptares Therapeutics Limited, Cambridge (GB)

(72) Inventors: Giles Albert Brown, Cambridge (GB); Barry John Teobald, Cambridge (GB); Benjamin Gerald Tehan, Cambridge (GB)

(73) Assignees: Heptares Therapeutics Limited, Cambridge (GB); Allergan Pharmaceuticals International Limited, Dublin (IE)

( * ) Notice: Subject to any disclaimer, the term of this patent is extended or adjusted under 35 U.S.C. 154(b) by 88 days.

(21) Appl. No.: 17/311,121

(22) PCT Filed: Dec. 9, 2019

(86) PCT No.: PCT/GB2019/053466
§ 371 (c)(1),
(2) Date: Jun. 4, 2021

(87) PCT Pub. No.: WO2020/115505
PCT Pub. Date: Jun. 11, 2020

(65) Prior Publication Data
US 2021/0387969 A1    Dec. 16, 2021

(30) Foreign Application Priority Data
Dec. 7, 2018 (GB) ..................... 1819960

(51) Int. Cl.
| C07D 403/04 | (2006.01) |
| C07D 403/14 | (2006.01) |
| C07D 413/04 | (2006.01) |
| C07D 451/02 | (2006.01) |
| C07D 451/04 | (2006.01) |
| C07D 451/14 | (2006.01) |

(52) U.S. Cl.
CPC ......... *C07D 403/04* (2013.01); *C07D 403/14* (2013.01); *C07D 413/04* (2013.01); *C07D 451/02* (2013.01); *C07D 451/04* (2013.01); *C07D 451/14* (2013.01)

(58) Field of Classification Search
CPC .. C07D 403/04; C07D 403/14; C07D 413/04; C07D 451/02; C07D 451/14
See application file for complete search history.

(56) References Cited

U.S. PATENT DOCUMENTS

| 5,446,051 A | 8/1995 | Ornstein |
| 5,852,029 A | 12/1998 | Fisher et al. |
| 5,854,245 A | 12/1998 | Duggan et al. |
| 6,335,341 B1 | 1/2002 | Johnson et al. |
| 6,387,930 B1 | 5/2002 | Baroudy et al. |
| 6,699,880 B1 | 3/2004 | Yamakawa et al. |
| 7,067,507 B2 | 6/2006 | Pulley et al. |
| 7,163,938 B2 | 1/2007 | Herron et al. |
| 7,524,852 B2 | 4/2009 | Arai et al. |
| 7,531,537 B2 | 5/2009 | Kawaguchi et al. |
| 8,119,661 B2 | 2/2012 | Cheng et al. |
| 8,476,289 B2 | 7/2013 | Freyne et al. |
| 9,067,951 B2 | 6/2015 | Ebel et al. |
| 9,187,451 B2 | 11/2015 | Congreve et al. |
| 9,266,857 B2 | 2/2016 | Brown et al. |
| 9,573,929 B2 | 2/2017 | Congreve et al. |
| 9,593,106 B2 | 3/2017 | Livermore et al. |
| 9,669,013 B2 | 6/2017 | Brown et al. |
| 9,670,183 B2 | 6/2017 | Brown et al. |
| 9,758,506 B2 | 9/2017 | Brown et al. |
| 9,907,805 B2 | 3/2018 | Congreve et al. |
| 9,926,297 B2 | 3/2018 | Brown et al. |
| 9,957,257 B2 | 5/2018 | Nirogi et al. |
| 9,975,890 B2 | 5/2018 | Brown et al. |
| 10,030,012 B2 | 7/2018 | Livermore et al. |
| 10,030,035 B2 | 7/2018 | Congreve et al. |
| 10,167,272 B2 | 1/2019 | Brown et al. |
| 10,167,284 B2 | 1/2019 | Congreve et al. |
| 10,196,380 B2 | 2/2019 | Brown et al. |
| 10,259,787 B2 | 4/2019 | Brown et al. |
| 10,259,802 B2 | 4/2019 | Brown et al. |
| 10,329,278 B2 | 6/2019 | Brown et al. |
| 10,351,545 B2 | 6/2019 | Brown et al. |
| 10,385,039 B2 | 8/2019 | Brown et al. |
| 10,413,553 B2 | 9/2019 | Congreve et al. |
| 10,428,088 B2 | 10/2019 | Congreve et al. |
| 10,501,483 B2 | 12/2019 | Dinh et al. |

(Continued)

FOREIGN PATENT DOCUMENTS

| CN | 1298391 | 6/2001 |
| EA | 002393 | 5/2016 |

(Continued)

OTHER PUBLICATIONS

Chen et al., Zoological Research, 2022, 43(6), pp. 1026-1040. (Year: 2022).*

(Continued)

*Primary Examiner* — Laura L Stockton
(74) *Attorney, Agent, or Firm* — Fish & Richardson P.C.

(57) ABSTRACT

This invention relates to compounds that are agonists of the muscarinic $M_1$ and/or $M_4$ receptor and which are useful in the treatment of diseases mediated by the muscarinic $M_1$ and $M_4$ receptors. Also provided are pharmaceutical compositions containing the compounds and the therapeutic uses of the compounds. Compounds provided are of formula where $X^1$; $X^2$; $R^1$ and $R^4$ are as defined herein.

(I)

15 Claims, No Drawings

(56) References Cited

U.S. PATENT DOCUMENTS

| | | |
|---|---|---|
| 10,548,884 B2 | 2/2020 | Brown et al. |
| 10,689,368 B2 | 6/2020 | Brown et al. |
| 10,738,029 B2 | 8/2020 | Brown et al. |
| 10,752,610 B2 | 8/2020 | Brown et al. |
| 10,759,751 B2 | 9/2020 | Brown et al. |
| 10,787,447 B2 | 9/2020 | Brown et al. |
| 10,858,352 B2 | 12/2020 | Brown et al. |
| 10,961,225 B2 | 3/2021 | Brown et al. |
| 10,973,832 B2 | 4/2021 | Congreve et al. |
| 11,014,880 B2 | 5/2021 | Brown et al. |
| 11,034,704 B2 | 6/2021 | Congreve et al. |
| 11,091,456 B2 | 8/2021 | Brown et al. |
| 11,208,396 B2 | 12/2021 | Brown et al. |
| 11,254,656 B2 | 2/2022 | Brown et al. |
| 11,319,312 B2 | 5/2022 | Brown et al. |
| 11,324,738 B2 | 5/2022 | Brown et al. |
| 11,352,342 B2 | 6/2022 | Brown et al. |
| 11,773,090 B2 | 10/2023 | Brown et al. |
| 2002/0156081 A1 | 10/2002 | Hirst et al. |
| 2003/0225271 A1 | 12/2003 | Emmanuel et al. |
| 2004/0171614 A1 | 9/2004 | Pissarnitski et al. |
| 2005/0085505 A1 | 4/2005 | Best et al. |
| 2005/0085506 A1 | 4/2005 | Pissarnitski et al. |
| 2005/0176703 A1 | 8/2005 | Gabriel et al. |
| 2006/0194844 A1 | 8/2006 | Sugawawa et al. |
| 2006/0276506 A1 | 12/2006 | Yu et al. |
| 2007/0043023 A1 | 2/2007 | Makings et al. |
| 2007/0054911 A1 | 3/2007 | Drutu et al. |
| 2007/0219218 A1 | 9/2007 | Yu et al. |
| 2008/0015179 A1 | 1/2008 | Makings et al. |
| 2009/0076078 A1 | 3/2009 | Cheng et al. |
| 2013/0012485 A1 | 1/2013 | Baeschlin et al. |
| 2014/0329803 A1 | 11/2014 | Congreve et al. |
| 2015/0232443 A1 | 8/2015 | Brown et al. |
| 2015/0376179 A1 | 12/2015 | Livermore et al. |
| 2016/0068508 A1 | 3/2016 | Congreve et al. |
| 2016/0128996 A1 | 5/2016 | Brown et al. |
| 2017/0015650 A1 | 1/2017 | Brown et al. |
| 2017/0037025 A1 | 2/2017 | Brown et al. |
| 2017/0096437 A1 | 4/2017 | Congreve et al. |
| 2017/0157139 A1 | 6/2017 | Congreve et al. |
| 2017/0183338 A1 | 6/2017 | Livermore et al. |
| 2017/0240530 A1 | 8/2017 | Brown et al. |
| 2017/0247369 A1 | 8/2017 | Brown et al. |
| 2018/0022726 A1 | 1/2018 | Brown et al. |
| 2018/0072727 A1 | 3/2018 | Congreve et al. |
| 2018/0105491 A1 | 4/2018 | Brown et al. |
| 2018/0153900 A1 | 6/2018 | Congreve et al. |
| 2018/0155315 A1 | 6/2018 | Brown et al. |
| 2018/0179184 A1 | 6/2018 | Brown et al. |
| 2018/0222885 A1 | 8/2018 | Brown et al. |
| 2018/0228791 A1 | 8/2018 | Brown et al. |
| 2018/0258085 A1 | 9/2018 | Brown et al. |
| 2018/0327426 A1 | 11/2018 | Congreve et al. |
| 2018/0362507 A1 | 12/2018 | Brown et al. |
| 2019/0112294 A1 | 4/2019 | Brown et al. |
| 2019/0202783 A1 | 7/2019 | Brown et al. |
| 2019/0270718 A1 | 9/2019 | Brown et al. |
| 2019/0276437 A1 | 9/2019 | Brown et al. |
| 2019/0337925 A1 | 11/2019 | Brown et al. |
| 2019/0389849 A1 | 12/2019 | Brown et al. |
| 2020/0002328 A1 | 1/2020 | Brown et al. |
| 2020/0017530 A1 | 1/2020 | Congreve et al. |
| 2020/0129496 A1 | 4/2020 | Brown et al. |
| 2020/0165220 A1 | 5/2020 | Brown et al. |
| 2020/0253982 A1 | 8/2020 | Congreve et al. |
| 2020/0290963 A1 | 9/2020 | Brown et al. |
| 2020/0325118 A1 | 10/2020 | Brown et al. |
| 2020/0354339 A1 | 11/2020 | Brown et al. |
| 2021/0002271 A1 | 1/2021 | Brown et al. |
| 2021/0040067 A1 | 2/2021 | Brown et al. |
| 2021/0101893 A1 | 4/2021 | Brown et al. |
| 2021/0353637 A1 | 11/2021 | Congreve et al. |
| 2022/0017504 A1 | 1/2022 | Brown et al. |
| 2022/0048928 A1 | 2/2022 | Congreve et al. |
| 2022/0213034 A1 | 7/2022 | Brown et al. |
| 2022/0298133 A1 | 9/2022 | Brown et al. |
| 2022/0380379 A1 | 12/2022 | Fieldhouse et al. |
| 2023/0002354 A1 | 1/2023 | Brown et al. |

FOREIGN PATENT DOCUMENTS

| | | |
|---|---|---|
| EP | 0034415 | 8/1981 |
| EP | 1221443 | 7/2002 |
| EP | 1647553 | 4/2006 |
| EP | 1679069 | 7/2006 |
| EP | 1900732 | 3/2008 |
| JP | S56110674 | 9/1981 |
| JP | H 11-501014 | 1/1999 |
| JP | 2000-501117 | 2/2000 |
| JP | 2000-502360 | 2/2000 |
| JP | 2003-529546 | 10/2003 |
| JP | 2006-509764 | 3/2006 |
| JP | 2006-516145 | 6/2006 |
| JP | 2006-219480 | 8/2006 |
| JP | 2008-521821 | 6/2008 |
| JP | 2009-527569 | 7/2009 |
| JP | 2013-010719 | 1/2013 |
| JP | 2017-505323 | 2/2017 |
| JP | 2018-508562 | 3/2018 |
| RU | 2323218 | 4/2008 |
| RU | 2008130094 | 1/2010 |
| WO | WO 94/15928 | 7/1994 |
| WO | WO 96/13262 | 5/1996 |
| WO | WO 97/16187 | 5/1997 |
| WO | WO 98/57641 | 12/1998 |
| WO | WO 99/32479 | 7/1999 |
| WO | WO 99/32481 | 7/1999 |
| WO | WO 99/32486 | 7/1999 |
| WO | WO 99/32489 | 7/1999 |
| WO | WO 2000/066141 | 11/2000 |
| WO | WO 2000/066559 | 11/2000 |
| WO | WO 2001/027104 | 4/2001 |
| WO | WO 2002/085890 | 10/2002 |
| WO | WO 2003/057672 | 7/2003 |
| WO | WO 2004/014853 | 2/2004 |
| WO | WO 2004/069828 | 8/2004 |
| WO | WO 2004/089942 | 10/2004 |
| WO | WO 2005/037269 | 4/2005 |
| WO | WO 2005/077369 | 8/2005 |
| WO | WO 2006/058294 | 6/2006 |
| WO | WO 2006/068904 | 6/2006 |
| WO | WO 2006/105035 | 10/2006 |
| WO | WO 2007/076070 | 7/2007 |
| WO | WO 2007/079164 | 7/2007 |
| WO | WO 2007/100664 | 9/2007 |
| WO | WO 2007/100670 | 9/2007 |
| WO | WO 2008/021375 | 2/2008 |
| WO | WO 2008/077597 | 7/2008 |
| WO | WO 2008/117229 | 10/2008 |
| WO | WO 2009/034380 | 3/2009 |
| WO | WO 2009/108117 | 9/2009 |
| WO | WO 2010/049146 | 5/2010 |
| WO | WO 2010/070032 | 6/2010 |
| WO | WO 2010/121046 | 10/2010 |
| WO | WO 2010/130945 | 11/2010 |
| WO | 2011/112825 A2 | 9/2011 |
| WO | WO 2011/133750 | 10/2011 |
| WO | WO 2011/137012 | 11/2011 |
| WO | WO 2011/143057 | 11/2011 |
| WO | WO 2011/150183 | 12/2011 |
| WO | WO 2012/037393 | 3/2012 |
| WO | WO 2012/125661 | 9/2012 |
| WO | 2013/072705 A1 | 5/2013 |
| WO | 2014/045031 A1 | 3/2014 |
| WO | 2014/122474 A1 | 8/2014 |
| WO | WO 2015/118342 | 8/2015 |
| WO | WO 2015/140559 | 9/2015 |
| WO | WO 2016/128990 | 8/2016 |
| WO | WO 2016/147011 | 9/2016 |
| WO | 2017/021730 A1 | 2/2017 |
| WO | WO 2017/021728 | 2/2017 |
| WO | WO 2017/021729 | 2/2017 |

(56) References Cited

FOREIGN PATENT DOCUMENTS

| WO | WO 2017/077292 | 5/2017 |
|----|----------------|--------|
| WO | WO 2018/069732 | 4/2018 |
| WO | WO 2018/229511 | 12/2018 |
| WO | WO 2019/243850 | 12/2019 |
| WO | WO 2019/243851 | 12/2019 |
| WO | WO 2020/115506 | 6/2020 |
| WO | WO 2022/129951 | 6/2022 |
| WO | WO 2022/189366 | 9/2022 |

OTHER PUBLICATIONS

Amal Chakraburtty, MD, "Psychotic Disorders" MedicineNet.com, Feb. 1, 2007. (Year: 2007).*
Melancon et al., Continued optimization of the MLPCN probe ML071 into highly potent agonists of the hM1 muscarinic acetylcholine receptor. Bioorg Med Chem Lett. May 15, 2012,22(10):3467-72.
International Search Report and Written Opinion for Application No. PCT/GB2019/053466, dated Feb. 12, 2020, 14 pages.
Bakker et al., "First-in-man study to investigate safety, pharmacokinetics and exploratory pharmacodynamics of HTL0018318, a novel M1-receptor partial agonist for the treatment of dementias," British Journal of Clinical Pharmacology, 2021, 87(7):2945-2955.
Bradley et al., "AC-260584, an orally bioavailable M1 muscarinic receptor allosteric agonist, improves cognitive performance in an animal model," Neuropharmacology, 2010, 58(2):365-373.
Broadley et al., "Muscarinic Receptor Agonists and Antagonists," Molecules, 2001, 6:142-193.
Cao et al., "Synthesis and Biological and Characterization of 1-methyl-1,2,5,6- tetrahydropyridy-1,2,5-thiadiazole Derivatives as Muscarinic agonists for treatment of Neurological Disorders," J Med Chem., 2003, 46(20):4273-4286.
Chapman et al., "The muscarinic M4 receptor is the functionally predominant subtype in rat and mouse striatum as demonstrated using [35S] GTPgammaS binding," European Journal of Pharmacology, 2011, 652:1-6.
Chung, "Aberrant phosphorylation in the pathogenesis of Alzheimer's disease," BMB reports, 2009, 42(8):467-474.
Conn et al., "Subtype-selective allosteric modulators of muscarinic receptors for the treatment of CNS disorders," Trends in Pharmacological Sciences, 2009, 30(3):148-155.
cnn.com [Online], "FDA panel backs late-stage Alzheimer's drug," available on or before Oct. 2, 2003, via Internet Archive: Wayback Machine URL<http://web.archive.org/web/20031002091517/http://www.cnn.com:80/2003/HEALTH/conditions/09/24/alzheimers.drug.ap/index.html>, retrieved on Oct. 21, 22, URL<http://www.cnn.com/2003/HEALTH/conditions/09/24/alzheimers.drug.ap/index.html>, 3 pages.
Fisher, "Cholinergic modulation of amyloid precursor protein processing with emphasis on M 1 muscarinic receptor: perspectives and challenges in treatment of Alzheimer's disease," J Neurochem., 2012, 120(Suppl. 1):22-33.
Foley et al., "The 5-HT(6) receptor antagonist SB-271046 reverses scopolamine- disrupted consolidation of a passive avoidance task and ameliorates spatial task deficits in aged rats," Neuropsychopharmacology, 2004, 29(1):93-100.
Foster et al., "Activation of M1 and M4 muscarinic receptors as potential treatments for Alzheimer's disease and schizophrenia," Neuropsychiatric Disease and Treatment, 2014, 10:183-191.
Gilles et al., "Pharmacological models in Alzheimer's disease research," Dialogues in Clinical Neuroscience, 2000, 2(3):247-255.
Hackam et al., "Translation of research evidence from animals to humans," JAMA, 2006, 296(14):1731-1732.
Hasselmo et al., "Modes and Models of Forebrain Cholinergic Neuromodulation of Cognition," Neuropsychopharmacology Reviews, 2011, 36:52-73.
Jordan, "Tamoxifen: a most unlikely pioneering medicine," Nat Rev Drug Discov., 2003, 2(3):205-213.
Jorden, "World Alzheimer Day: French Doctor Denounces Routine Alzheimer Medications," ZCommunications, retrieved on Dec. 20, 2015, retrieved from URL <https://zcomm.org/znetarticle/world-alzheimer-day-french-doctor-denounces-routine-alzheimer-medications/>, 4 pages.
Katz et al., "Transition from acute to chronic postsurgical pain: risk factors and protective factors," Expert Rev Neurother., May 2009, 9(5):723-744.
Kuduk et al., "Novel M1 allosteric ligands: a patent review," Expert Opin. Ther. Patents., 2012, 22(12): 1385-1398.
Lankin et al., "Protonated 3-fluoropiperidines: an unusual fluoro directing effect and a test for quantitative theories of solvation," J. Am. Chem. Soc., 1993, 115(8):3356-3357.
Lee et al., "Amyloid-beta in Alzheimer disease: the null versus the alternate hypotheses," J Pharmacol. Exp. Ther., Jun. 2007, 321(3):823-829.
Levey, "Muscarine acetylchloline receptor expression in memory circuits: implications for the treatment of Alzheimer disease," PNAS, 1996, 93(24): 13541-13546.
Lima et al., "Bioisosterism: A Useful Strategy for Molecular Modification and Drug Design," Curr Med Chem., 2005, 12:23-49.
Martino et al., "The M1/M4 preferring agonist xanomeline is analgesic in rodent models of chronic inflammatory and neuropathic pain via central site of action," Pain, 2011, 152:2852-2860.
Meanwell, "Synopsis of Some Recent Tactical Application of Bioisosteres in Drug Design," J Med Chem., 2011, 54(8):2529-2591.
Nirogi et al., "Synthesis and SAR of Imidazo[1,5-a]pyridine derivatives as 5-HT4 receptor partial agonists for the treatment of cognitive disorders associated with Alzheimer's disease," European Journal of Medicinal Chemistry, 2015, 103:289-301.
Osatuke et al., "Insight in schizophrenia: a review of etiological models and supporting research," Compr. Psychiatry, Jan.-Feb. 2008, 49(1):70-77.
Scarr, "Muscarinic receptors: their roles in disorders of the central nervous system and potential as therapeutic targets," CNS Neuroscience & Therapeutics, 2012, 18:369-379.
Snyder et al., "The Unexpected Diaxial Orientation of cis-3,5-Difluoropiperidine in Water: A Potent CF-NH Charge-Dipole Effect," J. Am. Chem. Soc., 2000, 122(3):544-545.
Tasker et al., "P110—Single and Multiple Dose Safety, Tolerability and Pharmacokinetics of the Selective M1 Receptor Partial Agonist HTL0018318 in Healthy Volunteers," The Journal of Prevention of Alzheimer's Disease, 2018, 5(1):S64-S65.
Tasker et al., "Single and multiple dose safety, tolerability and pharmacokinetics of the selective M1 receptor partial agonist HTL0018318 in healthy volunteers," Poster Presentation, Sosei Heptares, Nov. 2018, 2 pages.
Tecle et al., "Design and Synthesis of m1-Selective Muscarinic Agonists: (R)-(−)-(Z)-1-Azabicyclo[2.2.1 ]heptan-3-one, O-(3-(3'-Methoxyphenyl)-2-propynyl)-oxime Maleate (CI-1017), a Functionally m1-Selective Muscarinic Agonist," J Med Chem., 1998, 41(14):2524-2536.
Tietje et al., "Preclinical Characterization of A-582941: A Novel α7 Neuronal Nicotinic Receptor Agonist with Broad Spectrum Cognition-Enhancing Properties," CNS Neuroscience & Therapeutics, 2008, 14:65-82.
Toja et al., "1-Alkyl-1,2,S,6-tetrahydropyridine-3-carboxaldehyde-0-alkyl-oximes: a new class of potent orally active muscarinic agonists related to arecoline," Eur J Med Chem, 1991, 26:853-868.
Venkatesh et al., "Role of the development scientist in compound lead selection and optimization," J Pharm Sci., 2000, 89:145-154.
Confirmatory Assignment Cover Sheet for U.S. Appl. No. 16/450,261; and U.S. Appl. No. 17/024,085, executed on Oct. 10, 2023, recorded on Nov. 3, 2023, 4 pages.
Confirmatory Assignment Cover Sheet for U.S. Appl. No. 16/450,279; U.S. Appl. No. 17/069,070; U.S. Appl. No. 17/708,494; U.S. Appl. No. 17/958,599; and U.S. Appl. No. 18/133,036, executed on Oct. 10, 2023, recorded on Nov. 3, 2023, 4 pages.
Confirmatory Assignment Cover Sheet for U.S. Appl. No. 17/311,121, executed on Oct. 10, 2023, recorded on Nov. 3, 2023, 4 pages.

(56) References Cited

OTHER PUBLICATIONS

Confirmatory Assignment Cover Sheet for U.S. Appl. No. 17/874,564, executed on Oct. 10, 2023, recorded on Nov. 3, 2023, 5 pages.
Confirmatory Assignment Cover Sheet for U.S. Appl. No. 18/280,611, executed on Oct. 10, 2023, recorded on Nov. 3, 2023, 4 pages.
Sauerber et al., "Muscarinic cholinergic agonists and antagonists of the 3-(3-alkyl-1,2,4-oxadiazol-5-y1)-1,2,5,6-tetrahydropyridine type. Synthesis and structure-activity relationships," Journal of Medicinal Chemistry, Feb. 1, 1991, 34(2):687-692.
Showell et al., "Tetrahydropyridyloxadiazoles: semi-rigid muscarinic ligands," Journal of Medicinal Chemitry, Mar. 1, 1991, 34(3): 1086-1094.

* cited by examiner

BICYCLIC AZA COMPOUNDS AS MUSCARINIC $M_1$ AND/OR $M_4$ RECEPTOR AGONISTS

CROSS-REFERENCE TO RELATED APPLICATIONS

This application is a 35 U.S.C. § 371 national stage filing of International Application No. PCT/GB2019/053466, filed on Dec. 9, 2019, which claims priority to United Kingdom Application No. 1819960.4, filed on Dec. 7, 2018, the entire contents of each of which are incorporated herein by reference.

This invention relates to a class of novel heterocyclic compounds, their salts, pharmaceutical compositions containing them and their use in therapy of the human body. In particular, the invention is directed to a class of compounds, which are agonists of the muscarinic $M_1$ receptor and/or $M_4$ receptor, and hence are useful in the treatment of Alzheimer's Disease, schizophrenia, cognitive disorders and other diseases mediated by the muscarinic $M_1/M_4$ receptors, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 Br J Pharmacol). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 Br J Pharmacol).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 Science). In schizophrenia, which is also characterised by cognitive impairments, mAChR density is reduced in the pre-frontal cortex, hippocampus and caudate putamen of schizophrenic subjects (Dean et al., 2002 Mol Psychiatry). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (drugs.com/pro/donepezil; drugs.com/pro/rivastigmine).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm. Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidogenic and amyloidogenic. Cleavage of APP by γ-secretase is common to both pathways, but in the former APP is cleaved by an α-secretase to yield soluble APPα. The cleavage site is within the Aβ sequence, thereby precluding its formation. However, in the amyloidogenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 Neuron). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 Neurol).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 CNS Drug Rev). Muscarinic receptors have also been implicated in the neurobiology of addiction. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models. Muscarinic receptors are also involved in the control of movement and potentially represent novel treatments for movement disorders such as Parkinson's disease, ADHD, Huntingdon's disease, tourette's syndrome and other syndromes associated with dopaminergic dysfunction as an underlying pathogenetic factor driving disease. Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic side effects, including nausea, gastrointestinal pain, diarrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required.

Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes. WO2014/122474 relates to muscarinic M4 receptor agonist compounds.

The Invention

The present invention provides compounds having activity as muscarinic $M_1$ and/or $M_4$ receptor agonists. More particularly, the invention provides compounds that exhibit selectivity for the $M_1$ and/or $M_4$ receptor relative to the $M_2$ and $M_3$ receptor subtypes. Accordingly, in a first embodiment (Embodiment 1.1), the invention provides a compound of the formula (1):

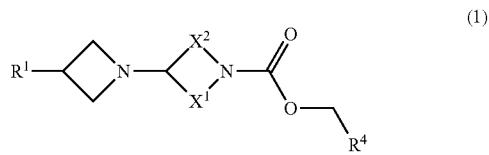

or a salt thereof, wherein:

$X^1$ and $X^2$ are saturated hydrocarbon groups which together contain a total of five to nine carbon atoms and zero or one oxygen atoms and which link together such that the moiety:

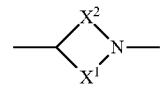

forms a monocyclic or bicyclic ring system optionally substituted with one or more fluorine atoms;

$R^1$ is selected from $COR^5$; $COOR^5$; $CONR^5R^6$; $C(=NR^5)R^6$; $OCOR^5$; $NR^7COR^5$; $NR^7CONR^5R^6$; $NR^7COOR^5$; $OCONR^5R^6$; $CH_2OR^5$; $CH_2NR^5R^6$; $CH_2COR^5$; $CH_2COOR^5$; $CH_2CONR^5R^6$; $CH_2C(=NR^5)R^6$; $CH_2OCOR^5$; $CH_2NR^7COR^5$; $CH_2NR^7CONR^5R^6$; $CH_2NR^7COOR^5$; $CH_2OCONR^5R^6$; $CH_2CH_2NR^5R^6$, an optionally substituted 5- or 6-membered ring containing 0, 1, 2 or 3 heteroatoms selected from O, N and S and oxidized forms thereof, or a $C_{1-6}$ non-aromatic hydrocarbon group which is optionally substituted with one to six fluorine atoms or which is optionally substituted with a 5- or 6-membered ring containing 0, 1, 2 or 3 heteroatoms selected from O, N and S and oxidized forms thereof and wherein one or two, but not all, carbon atoms of the hydrocarbon group may optionally be replaced by a heteroatom selected from O, N and S and oxidized forms thereof;

$R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof; and $R^5$, $R^6$ and $R^7$ are the same or different and each is independently selected from hydrogen, a non-aromatic $C_{1-6}$ hydrocarbon group optionally substituted with one or more fluorine atoms or optionally substituted with a 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 heteroatoms selected from O, N and S and oxidized forms thereof.

Particular and preferred compounds of the formula (1) are as defined in the following Embodiments 1.2 to 1.52:

1.2 A compound according to Embodiment 1.1 wherein $R^1$ is selected from $CH_2CONR^5R^6$; $OCONR^5R^6$ or a $C_{1-6}$ non-aromatic hydrocarbon group which is substituted with a 5- or 6-membered ring containing 0, 1, 2 or 3 heteroatoms selected from O, N and S and oxidized forms thereof.

1.3 A compound according to any one of Embodiments 1.1 or 1.2 wherein $R^1$ is selected from $CH_2CONR^5R^6$ or $OCONR^5R^6$.

1.4 A compound according to any one of Embodiments 1.1 to 1.3 wherein $R^1$ is $CH_2CONR^5R^6$.

1.5 A compound according to any one of Embodiments 1.1 to 1.3 wherein $R^1$ is $OCONR^5R^6$.

1.6 A compound according to Embodiment 1.1 wherein $R^5$, $R^6$ and $R^7$ are the same or different and each is independently selected from hydrogen, a non-aromatic $C_{1-6}$ hydrocarbon group optionally substituted with one or more fluorine atoms or optionally substituted with a 5- or 6-membered ring containing 0, 1, 2 or 3 heteroatoms selected from O, N and S and oxidized forms thereof.

1.7 A compound according to Embodiment 1.6 wherein $R^5$ is $C_rC_3$ alkyl.

1.8 A compound according to Embodiment 1.6 wherein $R^6$ is $C_rC_3$ alkyl.

1.9 A compound according to Embodiment 1.6 wherein $R^7$ is $C_rC_3$ alkyl.

1.10 A compound according to Embodiment 1.6 wherein any of $R^5$, $R^6$ and $R^7$ are selected from methyl, ethyl and isopropyl.

1.11 A compound according to Embodiment 1.6 wherein any of $R^5$, $R^6$ and $R^7$ are methyl.

1.12 A compound according to Embodiment 1.6 wherein any of $R^5$, $R^6$ and $R^7$ are ethyl.

1.13 A compound according to Embodiment 1.6 wherein any of $R^5$, $R^6$ and $R^7$ are isopropyl.

1.14 A compound according to Embodiment 1.1 wherein $R^1$ is selected from $CH_2CONR^5R^6$ or $OCONR^5R^6$, wherein $R^5$ and $R^6$ are selected from methyl, ethyl and isopropyl.

1.15 A compound according to Embodiment 1.1 wherein $R^5$ and $R^6$ are joined together to form an optionally substituted monocyclic or bicyclic ring containing 0, 1, 2 or 3 heteroatoms selected from O, N and S and oxidized forms thereof.

1.16 A compound according to Embodiment 1.1 wherein $R^1$ is selected from $CH_2CONR^5R^6$; $OCONR^5R^6$ or $CH_2CH_2NR^5R^6$, wherein $R^5$ and $R^6$ are joined together to form an optionally substituted monocyclic or bicyclic ring containing 0, 1, 2 or 3 heteroatoms selected from O, N and S and oxidized forms thereof.

1.17 A compound according to Embodiment 1.1 wherein $R^1$ is $CH_2CONR^5R^6$, wherein $R^5$ and $R^6$ are joined together to form an optionally substituted monocyclic or bicyclic ring containing 0, 1, 2 or 3 heteroatoms selected from O, N and S and oxidized forms thereof.

1.18 A compound according to Embodiment 1.1 wherein $R^1$ is $OCONR^5R^6$, wherein $R^5$ and $R^6$ are joined together to form an optionally substituted monocyclic or bicyclic ring containing 0, 1, 2 or 3 heteroatoms selected from O, N and S and oxidized forms thereof.

1.19 A compound according to any one of Embodiments 1.15 to 1.18 wherein $R^5$ and $R^6$ are joined to form a 4 to 7 membered ring containing 0 or 1 oxygen atoms.

1.20 A compound according to Embodiment 1.1 wherein $R^1$ is selected from:

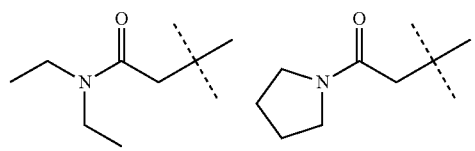

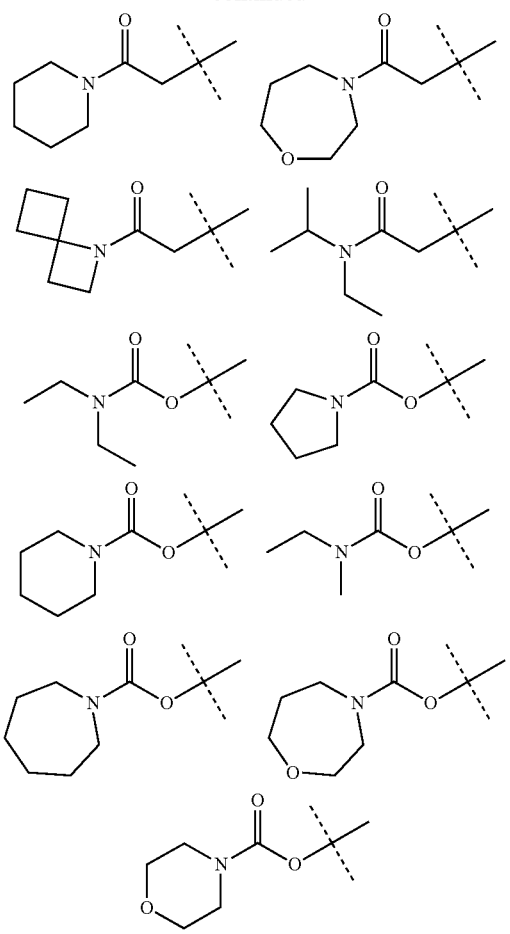

1.21 A compound according to any one of Embodiments 1.15 to 1.18 wherein $R^5$ and $R^6$ are joined together and $R^1$ is selected from:

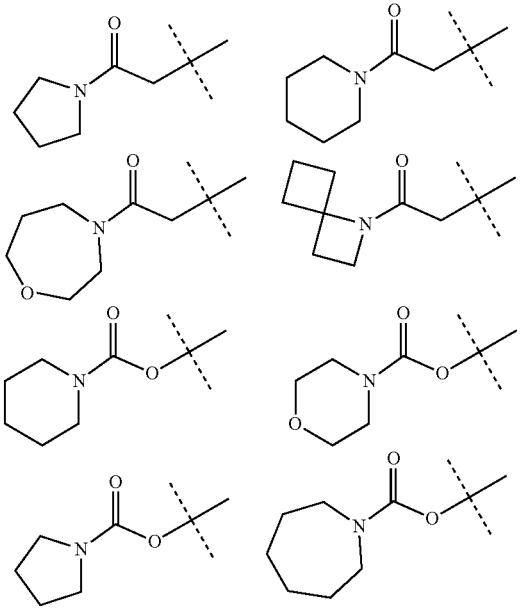

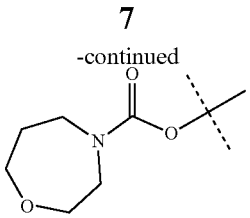

1.22 A compound according to any one of Embodiments 1.15 to 1.18 wherein $R^5$ and $R^6$ are joined together to form an azepane, pyrrolidine, piperidine, 1,4-oxazepane, 1-azaspiro[3.3]heptane or morpholine ring system.

1.23 A compound according to any one of Embodiments 1.1 to 1.22 wherein $R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof.

1.24 A compound according to any one of Embodiments 1.1 to 1.22 wherein $R^4$ is selected from H, methyl, ethyl, ethynyl and 1-propynyl.

1.25 A compound according to any one of Embodiments 1.1 to 1.22 wherein $R^4$ is H.

1.26 A compound according to any one of Embodiments 1.1 to 1.22 wherein $R^4$ is methyl.

1.27 A compound according to any one of Embodiments 1.1 to 1.26 wherein $X^1$ and $X^2$ are linked to form an 8-azabicyclo[3.2.1]octane, 9-azabicyclo[3.3.1]nonane, 6-azaspiro[3.4]octane, 2-azaspiro[3.4]octane, 2-azaspiro[3.3]heptane, 3-oxa-9-azabicyclo[3.3.1]nonane or 2-azabicyclo[2.2.2]octane ring system.

1.28 A compound according to any one of Embodiments 1.1 to 1.26 wherein the bicyclic ring system formed by the moiety:

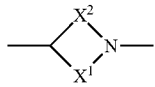

is selected from:

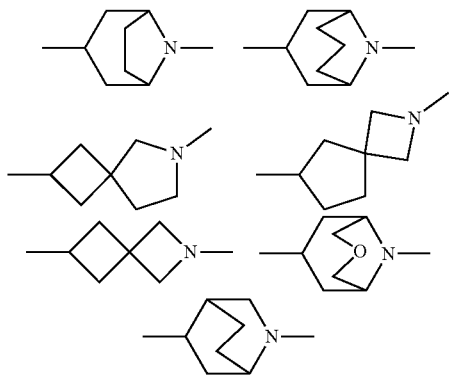

1.29 A compound according to any one of Embodiments 1.1 to 1.28 wherein the compound is selected from:
Ethyl-3-(3-(2-(diethylamino)-2-oxoethyl)azetidin-1-yl)-8-azabicyclo[3.2.1]octane-8-carboxylate;
Ethyl-3-(3-(2-(ethyl(isopropyl)amino)-2-oxoethyl)azetidin-1-yl)-8-azabicyclo[3.2.1]octane-8-carboxylate;
Ethyl-3-(3-(2-oxo-2-(1-azaspiro[3.3]heptan-1-yl)ethyl)azetidin-1-yl)-8-azabicyclo[3.2.1]octane-8-carboxylate;
Ethyl-3-(3-(2-oxo-2-(piperidin-1-yl)ethyl)azetidin-1-yl)-8-azabicyclo[3.2.1]octane-8-carboxylate;
Ethyl-5-(3-(2-(diethylamino)-2-oxoethyl)azetidin-1-yl)-2-azabicyclo[2.2.2]octane-2-carboxylate;
Ethyl-5-(3-(2-(ethyl(isopropyl)amino)-2-oxoethyl)azetidin-1-yl)-2-azabicyclo[2.2.2]octane-2-carboxylate;
Ethyl-5-(3-(2-oxo-2-(piperidin-1-yl)ethyl)azetidin-1-yl)-2-azabicyclo[2.2.2]octane-2-carboxylate;
Ethyl-5-(3-(2-(1,4-oxazepan-4-yl)-2-oxoethyl)azetidin-1-yl)-2-azabicyclo[2.2.2]octane-2-carboxylate;
Ethyl-5-(3-(2-oxo-2-(1-azaspiro[3.3]heptan-1-yl)ethyl)azetidin-1-yl)-2-azabicyclo[2.2.2]octane-2-carboxylate;
Ethyl-3-(3-(2-(diethylamino)-2-oxoethyl)azetidin-1-yl)-9-azabicyclo[3.3.1]nonane-9-carboxylate;
Ethyl-3-(3-(2-oxo-2-(pyrrolidin-1-yl)ethyl)azetidin-1-yl)-9-azabicyclo[3.3.1]nonane-9-carboxylate;
Ethyl-3-(3-(2-oxo-2-(piperidin-1-yl)ethyl)azetidin-1-yl)-9-azabicyclo[3.3.1]nonane-9-carboxylate;
Ethyl 6-(3-((diethylcarbamoyl)oxy)azetidin-1-yl)-2-azaspiro[3.3]heptane-2-carboxylate;
Ethyl 2-(3-((diethylcarbamoyl)oxy)azetidin-1-yl)-6-azaspiro[3.4]octane-6-carboxylate;
1-(6-(Ethoxycarbonyl)-6-azaspiro[3.4]octan-2-yl)azetidin-3-yl 1,4-oxazepane-4-carboxylate;
Ethyl 6-(3-((ethyl(methyl)carbamoyl)oxy)azetidin-1-yl)-2-azaspiro[3.4]octane-2-carboxylate;
Ethyl 6-(3-((diethylcarbamoyl)oxy)azetidin-1-yl)-2-azaspiro[3.4]octane-2-carboxylate;
Methyl 6-(3-((diethylcarbamoyl)oxy)azetidin-1-yl)-2-azaspiro[3.4]octane-2-carboxylate;
Ethyl 6-(3-((pyrrolidine-1-carbonyl)oxy)azetidin-1-yl)-2-azaspiro[3.4]octane-2-carboxylate;
1-(2-(Ethoxycarbonyl)-2-azaspiro[3.4]octan-6-yl)azetidin-3-yl morpholine-4-carboxylate;
1-(2-(Ethoxycarbonyl)-2-azaspiro[3.4]octan-6-yl)azetidin-3-yl 1,4-oxazepane-4-carboxylate;
Ethyl 3-(3-((azepane-1-carbonyl)oxy)azetidin-1-yl)-8-azabicyclo[3.2.1]octane-8-carboxylate;
1-(8-(Ethoxycarbonyl)-8-azabicyclo[3.2.1]octan-3-yl)azetidin-3-yl 1,4-oxazepane-4-carboxylate;
Ethyl 5-(3-((diethylcarbamoyl)oxy)azetidin-1-yl)-2-azabicyclo[2.2.2]octane-2-carboxylate;
Ethyl 5-(3-((pyrrolidine-1-carbonyl)oxy)azetidin-1-yl)-2-azabicyclo[2.2.2]octane-2-carboxylate;
Ethyl 5-(3-((piperidine-1-carbonyl)oxy)azetidin-1-yl)-2-azabicyclo[2.2.2]octane-2-carboxylate;
Ethyl 5-(3-((azepane-1-carbonyl)oxy)azetidin-1-yl)-2-azabicyclo[2.2.2]octane-2-carboxylate;
1-(2-(Ethoxycarbonyl)-2-azabicyclo[2.2.2]octan-5-yl)azetidin-3-yl 1,4-oxazepane-4-carboxylate;
Ethyl 3-(3-((diethylcarbamoyl)oxy)azetidin-1-yl)-9-azabicyclo[3.3.1]nonane-9-carboxylate;
Ethyl 7-(3-((azepane-1-carbonyl)oxy)azetidin-1-yl)-3-oxa-9-azabicyclo[3.3.1]nonane-9-carboxylate;
or a salt thereof.

1.30 A compound according to Embodiment 1.1 which is as defined in any one of Examples 1 to 31.

1.31 A compound according to any one of Embodiments 1.1 to 1.30 having a molecular weight of less than 550, for example less than 500, or less than 450.

1.32 A compound according to any one of Embodiments 1.1 to 1.31 which is in the form of a salt.

1.33 A compound according to Embodiment 1.32 wherein the salt is an acid addition salt.

1.34 A compound according to Embodiment 1.32 or Embodiment 1.33 wherein the salt is a pharmaceutically acceptable salt.

Definitions

In this application, the following definitions apply, unless indicated otherwise.

The term "treatment", in relation to the uses of the compounds of the formula (1), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "alkyl", "heterocyclic" and "ether" are used in their conventional sense (e.g. as defined in the IUPAC Gold Book) unless indicated otherwise.

The term "monocyclic" as used herein refers to an arrangement of atoms arranged in such a way as to form a single ring structure. The term "bicyclic" as used herein refers to an arrangement of atoms arranged in such a way as to form two joined rings. A bicyclic compound can be carbocyclic, or heterocyclic. Moreover, the two rings can both be aliphatic, or can be aromatic, or a combination of aliphatic and aromatic.

In the definitions of $X^1$, $X^2$, $R^1$ and $R^4$ above, where stated, one or two but not all, carbon atoms of the non-aromatic hydrocarbon groups may optionally be replaced by a heteroatom selected from O and N. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—S(O)$_2$—$CH_2$—, replacement of a carbon atom in a —$CH_2$—$CH_2$—$CH_2$-chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) can exist in the form of salts, for example acid addition salts or, in certain cases salts of organic and inorganic bases such as carboxylate, sulfonate and phosphate salts. All such salts are within the scope of this invention, and references to compounds of the formula (1) include the salt forms of the compounds as defined in Embodiments 1.32 to 1.34.

The salts are typically acid addition salts.

The salts of the present invention can be synthesized from the parent compound that contains a basic or acidic moiety by conventional chemical methods such as methods described in *Pharmaceutical Salts; Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.33) may be formed with a wide variety of acids, both inorganic and organic. Examples of acid addition salts falling within Embodiment 1.33 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, β-toluenesulfonic, undecylenic and valeric acids, as well as acylated amino acids and cation exchange resins.

Where the compounds of the formula (1) contain an amine function, these may form quaternary ammonium salts, for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.35), the invention provides a geometric isomer of a compound according to any one of Embodiments 1.1 to 1.34.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.36) the invention provides a compound according to any one of Embodiments 1.1 to 1.35 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.37), the invention provides compositions containing a compound according to Embodiment 1.36 having one or more chiral centres, wherein at least 55% (e.g. at least 60%, 65%, 70%, 75%, 80%, 85%, 90% or 95%) of the compound of Embodiment 1.35 is present as a single optical isomer (e.g. enantiomer or diastereoisomer).

In one general embodiment (Embodiment 1.38), 99% or more (e.g. substantially all) of the total amount of the compound (or compound for use) of Embodiment 1.36 is present as a single optical isomer.

For example, in one embodiment (Embodiment 1.39) the compound is present as a single enantiomer.

In another embodiment (Embodiment 1.40), the compound is present as a single diastereoisomer.

The invention also provides mixtures of optical isomers, which may be racemic or non-racemic. Thus, the invention provides:

1.41 A compound according to Embodiment 1.36 which is in the form of a racemic mixture of optical isomers.

1.42 A compound according to Embodiment 1.36 which is in the form of a non-racemic mixture of optical isomers.

Isotopes

The compounds of the invention as defined in any one of Embodiments 1.1 to 1.42 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.43), the compound of any one of Embodiments 1.1 to 1.42 contains no radioactive isotopes. Such compounds are preferred for therapeutic use. In another embodiment (Embodiment 1.44), however, the compound of any one of Embodiments 1.1 to 1.42 may contain one or more radioisotopes. Compounds containing such radioisotopes may be useful in a diagnostic context.

Solvates

Compounds of the formula (1) as defined in any one of Embodiments 1.1 to 1.44 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and di hydrates.

Accordingly, in further embodiments 1.45 and 1.46, the invention provides:

1.45 A compound according to any one of Embodiments 1.1 to 1.44 in the form of a solvate.

1.46 A compound according to Embodiment 1.45 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3. Alternatively, rather than existing as a hydrate, the compound of the invention may be anhydrous. Therefore, in another embodiment (Embodiment 1.47), the invention provides a compound as defined in any one of Embodiments 1.1 to 1.45 in an anhydrous form (e.g. anhydrous crystalline form).

Crystalline and Amorphous Forms

The compounds of any one of Embodiments 1.1 to 1.47 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.48 A compound according to any one of Embodiments 1.1 to 1.47 in a crystalline form.

1.49 A compound according to any one of Embodiments 1.1 to 1.47 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.50 A compound according to any one of Embodiments 1.1 to 1.47 which is in an amorphous form.

Prodrugs

The compounds of the formula (1) as defined in any one of Embodiments 1.1 to 1.44 may be presented in the form of a pro-drug. By "prodrugs" is meant for example any compound that is converted in vivo into a biologically active compound of the formula (1), as defined in any one of Embodiments 1.1 to 1.44.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.51), the invention provides a pro-drug of a compound as defined in any one of Embodiments 1.1 to 1.44 wherein the compound contains a functional group which is convertible under physiological conditions to form a hydroxyl group or amino group.

Complexes and Clathrates

Also encompassed by formula (1) in Embodiments 1.1 to 1.51 are complexes (e.g. inclusion complexes or clathrates with compounds such as cyclodextrins, or complexes with metals) of the compounds of Embodiments 1.1 to 1.51.

Accordingly, in another embodiment (Embodiment 1.52), the invention provides a compound according to any one of Embodiments 1.1 to 1.51 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptor relative to the $M_2$ and $M_3$ receptor subtypes. Compounds of the invention are neither agonists nor antagonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention have activity at both the $M_1$ and $M_4$ receptors. Accordingly, in Embodiments 2.1 to 2.21, the invention provides:

2.1 A compound according to any one of Embodiments 1.1 to 1.52 for use in medicine.

2.2 A compound according to any one of Embodiments 1.1 to 1.52 for use as a muscarinic $M_1$, $M_4$ or $M_1$ and $M_4$ receptor agonist.

2.3 A compound according to any one of Embodiments 1.1 to 1.52 which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

2.4 A compound according to Embodiment 2.3 which is a muscarinic $M_1$ receptor agonist having a $pEC_{50}$ greater than 7.0.

2.5 A compound according to Embodiment 2.3 or Embodiment 2.4 having an $E_{max}$ of at least 90 against the $M_1$ receptor.

2.6 A compound according to any one of Embodiments 1.1 to 1.52 which is a muscarinic $M_1$ and/or $M_4$ receptor agonist having a $pEC_{50}$ in the range from 6.0 to 8.7 and an $E_{max}$ of at least 60 against the $M_4$ receptor in the assay of Example A herein or an assay substantially similar thereto.

2.7 A compound according to any one of Embodiments 1.1 to 1.52 which is a muscarinic $M_1$ and/or $M_4$ receptor agonist having a $pEC_{50}$ in the range from 6.0 to 8.1 and an $E_{max}$ of at least 90 against the $M_4$ receptor in the assay of Example A herein or an assay substantially similar thereto.

2.8 A compound according to Embodiment 2.6 which is a muscarinic $M_4$ receptor agonist having a $pEC_{50}$ in the range from 7.5 to 8.7.

2.9 A compound according to Embodiment 2.7 which is a muscarinic $M_4$ receptor agonist having a $pEC_{50}$ in the range from 6.5 to 7.5.

2.10 A compound according to Embodiment 2.6 or Embodiment 2.8 having an $E_{max}$ of at least 75 against the $M_4$ receptor.

2.11 A compound according to Embodiment 2.7 or Embodiment 2.9 having an $E_{max}$ of at least 95 against the $M_4$ receptor.

2.12 A compound according to any one of Embodiments 2.3 to 2.11 which is selective for the $M_1$ and $M_4$ receptor compared to the muscarinic $M_2$ and $M_3$ receptors.

2.13 A compound according to Embodiment 2.12 which is selective for the $M_1$ receptor compared to the muscarinic $M_2$ and $M_3$ receptors.

2.14 A compound according to Embodiment 2.12 which is selective for the $M_4$ receptor compared to the muscarinic $M_2$ and $M_3$ receptors.

2.15 A compound according to any one of Embodiments 2.3 to 2.5 which is selective for the $M_1$ receptor compared to the muscarinic $M_2$, $M_3$ and $M_4$ receptors.

2.16 A compound according to any one of Embodiments 2.3 to 2.5 which is selective for the $M_4$ receptor compared to the muscarinic $M_1$, $M_2$ and $M_3$ receptors.

2.17 A compound according to any one of Embodiments 2.3 to 2.16 which has a $pEC_{50}$ of less than 5 and an $E_{max}$ of less than 50 against the muscarinic $M_2$ and $M_3$ receptor subtypes.

2.18 A compound according to Embodiment 2.17 which has a $pEC_{50}$ of less than 4.5 and/or an $E_{max}$ of less than 30 against the muscarinic $M_2$ and $M_3$ receptor subtypes.

2.19 A compound according to any one of Embodiments 1.1 to 1.52 and Embodiments 2.3 to 2.16 for use in the treatment of a disease or condition mediated by the muscarinic $M_1$ receptor.

2.20 A compound according to any one of Embodiments 1.1 to 1.52 and Embodiments 2.3 to 2.16 for use in the treatment of a disease or condition mediated by the muscarinic $M_4$ receptor.

2.21 A compound according to any one of Embodiments 1.1 to 1.52 and Embodiments 2.3 to 2.16 for use in the treatment of a disease or condition mediated by the muscarinic $M_1$ and $M_4$ receptor.

By virtue of their muscarinic $M_1$, $M_4$ or $M_1$ and $M_4$ receptor agonist activity, compounds of the invention can be used in the treatment of Alzheimer's disease, schizophrenia and other psychotic disorders, cognitive disorders and other diseases mediated by the muscarinic $M_1$ or $M_1$ and $M_4$ receptor, and can also be used in the treatment of various types of pain.

Accordingly, in Embodiments 2.22 to 2.43, the invention provides:

2.22 A compound according to any one of Embodiments 1.1 to 1.52 for use in the treatment of a cognitive disorder or psychotic disorder.

2.23 A compound for use according to Embodiment 2.22 wherein the cognitive disorder or psychotic disorder comprises, arises from or is associated with a condition selected from cognitive impairment, Mild Cognitive Impairment (including mild cognitive impairment due to Alzhimer's disease and/or prodromal Alzheimer's disease), frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease (including prodromal Alzheimer's disease and stages 1, 2, and 3 early Alzheimer's disease as defined by the US Food and Drug Admistration's "Early Alzheimer's disease: Developing Drugs for Treatment" available at fda.gov/downloads/Drugs/GuidanceComplianceRegulatorylnformation/Guidances/UC M596728.pdf), progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, AIDS-related dementia or other dementia states such as multi-infarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and and schizo-affective disorder.

2.24 A compound according to any one of Embodiments 1.1 to 1.52 for use in the treatment of Alzheimer's disease.

2.25 A compound according to any one of Embodiments 1.1 to 1.52 for use in the treatment of Schizophrenia.

2.26 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.52.

2.27 A method according to Embodiment 2.26 wherein the cognitive disorder comprises, arises from or is associated with a condition as defined in Embodiment 2.19.

2.28 A method according to Embodiment 2.27 wherein the cognitive disorder arises from or is associated with Alzheimer's disease.

2.29 A method according to Embodiment 2.27 wherein the cognitive disorder is Schizophrenia.

2.30 The use of a compound according to any one of Embodiments 1.1 to 1.52 for the manufacture of a medicament for the treatment of a cognitive disorder.

2.31 The use according to Embodiment 2.30 wherein the cognitive disorder comprises, arises from or is associated with a condition as defined in Embodiment 2.23.

2.32 The use according to Embodiment 2.31 wherein the cognitive disorder arises from or is associated with Alzheimer's disease.

2.33 The use according to Embodiment 2.32 wherein the cognitive disorder is Schizophrenia.

2.34 A compound according to any one of Embodiments 1.1 to 1.52 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.35 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.52.

2.36 A compound according to any one of Embodiments 1.1 to 1.52 for the treatment of peripheral disorders such as reduction of intra ocular pressure in Glaucoma and treatment of dry eyes and dry mouth including Sjogren's Syndrome.

2.37 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.52.

2.38 The use of a compound according to any one of Embodiments 1.1 to 1.52 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.39 The use of a compound according to any one of Embodiments 1.1 to 1.52 for the treatment of skin lesions for example due to pemphigus vulgaris, dermatitis herpetiformis, pemphigoid and other blistering skin conditions.

2.40 The use of a compound according to any one of Embodiments 1.1 to 1.52 for treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.41 The use of a compound according to any one of Embodiments 1.1 to 1.52 for the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.42 The use of a compound according to any one of Embodiments 1.1 to 1.52 for the treatment of addiction.

2.43 The use of a compound according to any one of Embodiments 1.1 to 1.52 for the treatment of movement disorders such as Parkinson's disease, ADHD, Huntingdon's disease, tourette's syndrome and other syndromes associated with dopaminergic dysfunction as an underlying pathogenetic factor driving disease.

2.44 The use of a compound according to any one of Embodiments 1.1 to 1.52 for the treatment of behavioural and psychological symptoms of dementia (BPSD; including agitation, verbal aggressiveness, physical aggressiveness, depression, anxiety, abnormal motor behaviour, elated mood, irritability, apathy, disinhibition, impulsivity. delusions, hallucinations, sleep changes, and appetite changes).

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.52, which process comprises:

(A) the reaction of a compound of the formula (10):

(10)

with a compound of the formula (11):

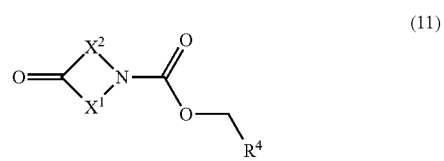

(11)

under reductive amination conditions; wherein $R^1$, $R^4$, $X^1$, and $X^2$ are as defined in any one of Embodiments 1.1 to 1.52; or (B) the reaction of a compound of formula (12):

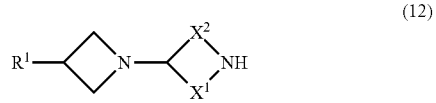

(12)

with a compound of the formula Cl—C(=O)—O—CH$_2$—R$^4$; wherein $R^1$, $R^4$, $X^1$ and $X^2$ are as defined in any one of Embodiments 1.1 to 1.52; or (C) when it is required to prepare a compound of formula (1) wherein $R^1$ comprises $CH_2CONR^5R^6$:

the reaction of a compound of the formula (13):

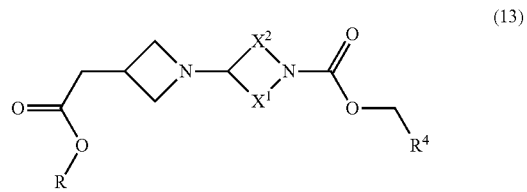

(13)

with an amine of the formula $R^5R^6NH$; wherein R represents a suitable group such as methyl- or ethyl- and $R^4$, $R^5$, $R^6$, $X^1$ and $X^2$ are as defined in any one of Embodiments 1.1 to 1.52; or (D) when it is required to prepare a compound of formula (1) wherein $R^1$ comprises $CH_2CONR^5R^6$:

the reaction of a compound of the formula (14):

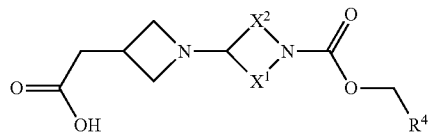

(14)

with an amine of the formula $R^5R^6NH$; wherein $R^4$, $R^5$, $R^6$, $X^1$ and $X^2$ are as defined in any one of Embodiments 1.1 to 1.52; or (E) when it is required to prepare a compound of formula (1) wherein $R^1$ comprises $OCONR^5R^6$:

the reaction of a compound of the formula (15):

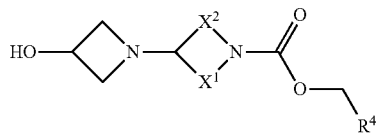

(15)

with an amine of the formula $R^5R^6NH$; wherein $R^4$, $R^5$, $R^6$, $X^1$ and $X^2$ are as defined in any one of Embodiments 1.1 to 1.52;

and optionally:

(F) converting one compound of the formula (1) to another compound of the formula (1).

In process variant (A), the amine (10) is reacted with the ketone (11) under reductive amination conditions. The reductive amination reaction is typically carried out at ambient temperature to mild heating (e.g. at a temperature of about 20° C. to about 70° C.) using a borohydride reducing agent such as sodium triacetoxy-borohydride (STAB) in a solvent such as dichloromethane (DCM), dichloroethane (DCE), N,N-dimethylformamide (DMF) or methanol (MeOH) containing an acid such as acetic acid (AcOH) or trifluoroacetic acid (TFA), or sodium cyanoborohydride (NaCNBH$_3$) in combination with zinc chloride (ZnCl$_2$) in a solvent such as MeOH, or STAB in a solvent such as DCM or DCE containing an acid such as AcOH or TFA in combination with titanium tetraisopropoxide (Ti(O$^i$Pr)$_4$). Optionally, the amine (10) may be present in the reaction as an acid salt such as a hydrogen chloride (HCl), hydrogen bromide (HBr) or a TFA salt, optionally in the presence of a tertiary base such as triethylamine (TEA) or N,N-diisopropylamine (DIPEA).

Amines of formula (10) may be commercially available, or alternatively may be prepared by simple methods well known to the skilled person. For example, when it is necessary to prepare a compound of formula (1) wherein $R^1$ comprises $CH_2CONR^5R^6$, wherein $R^5$ and $R^6$ are as defined in any one of Embodiments 1.1 to 1.52, amines of the formula (10) can be prepared by the sequence of reactions shown in Scheme 1 below:

Scheme 1

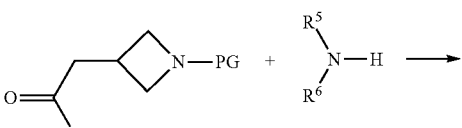

(16)

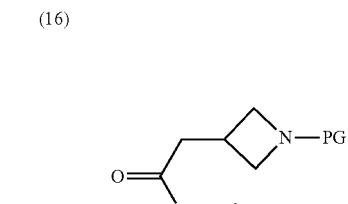

(17)

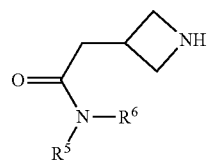

(18)

Thus, a protected amino ester (16), wherein R represents a suitable group such as methyl- or ethyl- and the protecting group PG represents a suitable protecting group such as tert-butyloxycarbonyl (BOC), is reacted with an amine of the formula $R^5R^6NH$, wherein $R^5$ and $R^6$ are as defined in any one of Embodiments 1.1 to 1.52 under conditions suitable to effect formation of protected amino amide (17). Typically, such conditions are reaction at a temperature between about 0° C. to about 110° C. in a solvent such as toluene in combination with a reagent such as trimethylaluminium (Me3Al), optionally in the presence of a tertiary base such as TEA or DIPEA. It will be well known to the skilled person that other suitable conditions exist to effect formation of protected amino amide (17) from protected amino ester (16) and amine $R^5R^6NH$, such as reaction in the presence of isopropylmagnesium chloride (iPrMgCl) in a suitable solvent, or direct heating, optionally in the presence of a suitable solvent. Once the protected amino amide (17) is formed, the protecting group PG can be removed using suitable conditions to form amine (18). For example, when the protecting group PG is BOC, then suitable conditions to effect its removal might be reaction with an acid such as HCl in a solvent such as 1,4-dioxane or diethyl ether (Et2O), or TFA in a solvent such as DCM.

Alternatively, protected amino amide (17) can be prepared by the sequence of reactions shown in Scheme 2 below:

Scheme 2

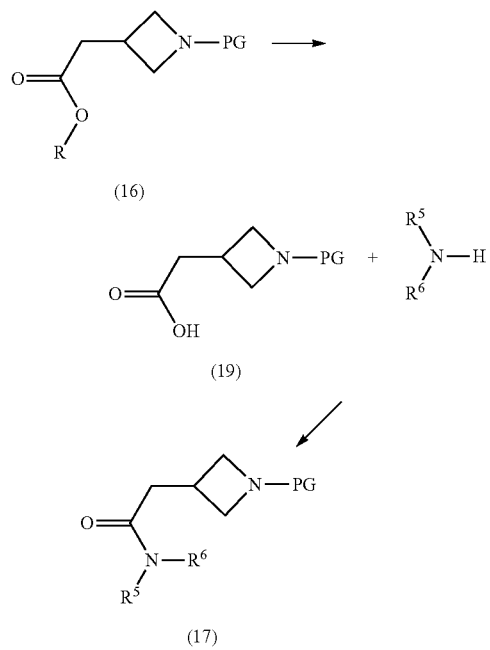

Scheme 3

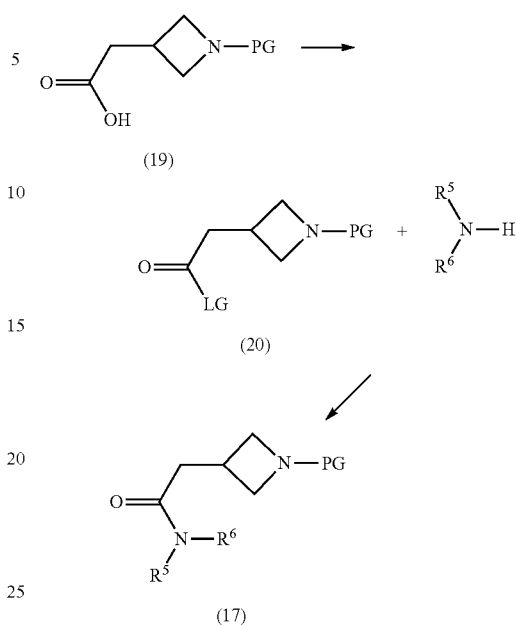

Thus, a protected amino ester (16), wherein R represents a suitable group such as methyl- or ethyl- and the protecting group PG represents a suitable protecting group such as BOC, is reacted under conditions suitable to effect hydrolysis of the ester to form protected amino acid (19). Typically, such conditions are reaction with a reagent such as lithium hydroxide (LiOH), sodium hydroxide (NaOH) or potassium hydroxide (KOH) in a solvent such as tetrahydrofuran (THF), MeOH, ethanol (EtOH), water (H$_2$O) or a combination of two or more of the aforementioned solvents, at a temperature of between about 0° C. to about 100° C. Once formed, the protected amino acid (19), is reacted with an amine of the formula R$^5$R$^6$NH, wherein R$^5$ and R$^6$ are as defined in any one of Embodiments 1.1 to 1.52, under conditions suitable to effect formation of protected amino amide (17). It will be well known to the skilled person that many suitable conditions exist in the art to effect formation of protected amino amide (18) from protected amino acid (19) and amine R$^5$R$^6$NH, for example reaction with an amide coupling reagent such as diisopropylcarbodiimide (DIC), ethyl-(N',N'-dimethylamino)propylcarbodiimide hydrochloride (EDC), (benzotriazol-1-yloxy)tripyrrolidinophosphonium hexafluorophosphate (PyBOP), 0-(7-azabenzotriazol-1-yl)-N,N,N',N'-tetramethyluronium hexafluorophosphate (HATU), (1-cyano-2-ethoxy-2-oxoethylidenaminooxy)dimethylamino-morpholino-carbenium hexafluorophosphate (COMU) or 2,4,6-tripropyl-1,3,5,2,4,6-trioxatriphosphorinane-2,4,6-trioxide (T3P), optionally in the presence of a tertiary base such as TEA or DIPEA, optionally in the presence of 1-hydroxybenzotriazole (HOBt), in a solvent such as DCM, THF or DMF, at a temperature between about 0° C. to about 100° C.

Alternatively, protected amino amide (17), can be prepared by the sequence of reactions shown in Scheme 3 below.

Thus protected amino acid (19), wherein the protecting group PG represents a suitable protecting group such as BOC, can be reacted under conditions suitable to effect formation of protected intermediate (20), wherein LG represents a suitable leaving group such as chloride (Cl), 1-imidazole, or RO(C═O)O (wherein R represents a group such as ethyl- or isobutyl-). Typically, such conditions are reaction with a reagent such as oxalyl chloride or thionyl chloride (LG=Cl), 1,1'-carbonyldiimidazole (CDI) (LG=1-imidazole) or ethyl- or isobutyl-chloroformate (LG=RO (C═O)O), optionally in the presence of a tertiary base such as TEA or DIPEA, optionally in the presence of a catalyst such as DMF, in a suitable solvent such as DCM, THF or DMF. Once formed, the protected intermediate (20), is reacted with an amine of the formula R$^5$R$^6$NH, wherein R$^5$ and R$^6$ are as defined in any one of Embodiments 1.1 to 1.52 under conditions suitable to effect formation of protected amino amide (17). Typically, such conditions are reaction at a temperature between about 0° C. to about 100° C. in a solvent such as DCM, THF or DMF, optionally in the presence of a tertiary base such as TEA or DIPEA.

Alternatively, when it is necessary to prepare a a compound of formula (1) wherein R$^1$ comprises OCONR$^5$R$^6$, wherein R$^5$ and R$^6$ are as defined in any one of Embodiments 1.1 to 1.52, amines of the formula (10) can be prepared by the sequence of reactions shown in Scheme 4 below:

Scheme 4

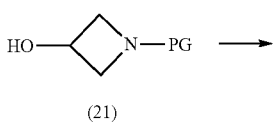

(21)

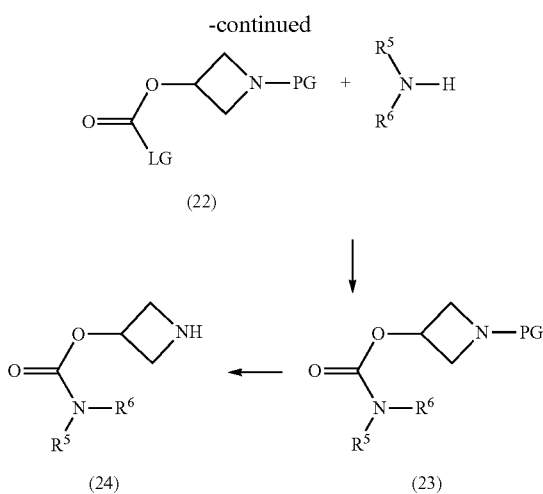

Thus a protected amino alcohol (21), wherein the protecting group PG represents a suitable protecting group such as BOC, can be reacted under conditions suitable to effect formation of protected intermediate (22), wherein LG represents a suitable leaving group such as Cl, 1-imidazole, or 4-nitrophenol. Typically, such conditions are reaction with a reagent such as phosgene or triphosgene (LG=Cl), CDI (LG=1-imidazole) or 4-nitrophenyl-chloroformate (LG=4-nitrophenol), optionally in the presence of a tertiary base such as TEA or DIPEA, in a suitable solvent such as DCM, THF or DMF. Once formed, the protected intermediate (22), is reacted with an amine of the formula $R^5R^6NH$, wherein $R^5$ and $R^6$ are as defined in any one of Embodiments 1.1 to 1.52 under conditions suitable to effect formation of protected amino carbamate (23). Typically, such conditions are reaction at a temperature between about 0° C. to about 100° C. in a solvent such as DCM, THF or DMF, optionally in the presence of a tertiary base such as TEA or DIPEA.

Ketones of the formula (11) can be prepared by the sequence of reactions shown in Scheme 5 below:

Scheme 5

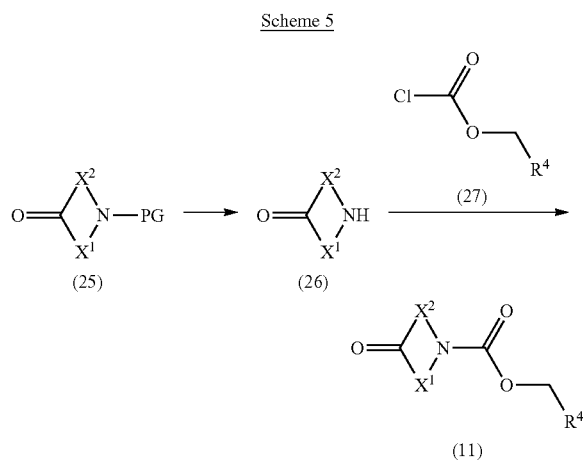

Thus, a protected amino ketone (25), wherein $X^1$ and $X^2$ are as defined in any one of Embodiments 1.1 to 1.52 and PG represents a suitable protecting group such as BOC or CBZ, can be deprotected to give amino ketone (26). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ then suitable conditions to effect its removal might be reaction with $H_2$ in the presence of a palladium on carbon (Pd/C) catalyst in a solvent such as EtOH at a temperature of about 20° C. to about 80° C. Once formed, amino ketone (26) can be reacted with chloroformate (27), wherein $R^4$ is as defined in any one of Embodiments 1.1 to 1.52, under suitable conditions to form ketone (11). Typically, such conditions are reaction at a temperature between about 0° C. to about 50° C. in a solvent such as DCM, THF or DMF, optionally in the presence of a tertiary base such as TEA or DIPEA.

In process variant (B), the compound of formula (12) is typically reacted with a compound of formula Cl—C (=O)—O—$CH_2$—$R^4$, wherein $R^4$ is as defined in any one of Embodiments 1.1 to 1.52, at a temperature between about 0° C. to about 50° C. in a solvent such as DCM, THF or DMF, optionally in the presence of a tertiary base such as TEA or DIPEA.

Compounds of formula (12) can be prepared by the sequence of reactions shown in Scheme 6 below:

Scheme 6

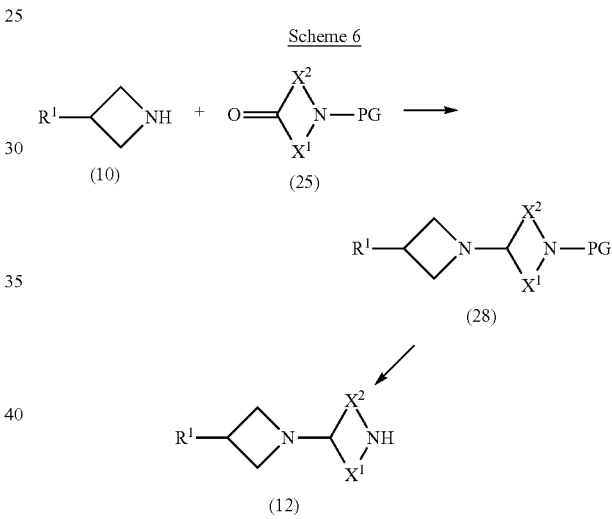

Thus, a compound of formula (10), wherein $R^1$ is as defined in any one of Embodiments 1.1 to 1.52, is reacted with a compound of formula (25), wherein $X^1$ and $X^2$ are as defined in any one of Embodiments 1.1 to 1.52 and PG represents a suitable protecting group such as BOC or CBZ, under reductive amination conditions to form a compound of formula (28). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or $NaCNBH_3$ in combination with $ZnCl_2$ in a solvent such as MeOH, or STAB in a solvent such as DCM or DCE containing an acid such as AcOH or TFA in combination with $Ti(OiPr)_4$. Optionally, compound (10) may be present in the reaction as an acid salt such as an HCl, HBr or a TFA salt, optionally in the presence of a tertiary base such as TEA or DIPEA. Once formed, the protecting group PG can be removed from a compound of formula (28) to form a compound of formula (12). For example, when the protecting group PG is BOC, then suitable conditions to effect its removal might be reaction with an acid such as HCl in a solvent such as 1,4-dioxane or Et$_2$O, or TFA in a solvent such as DCM. Alternatively, when the protecting group PG is CBZ then suitable conditions to effect its removal might be reaction with H$_2$ in the presence of a Pd/C catalyst in a solvent such as EtOH at a temperature of about 20° C. to about 80° C.

In process variant (C), the compound of formula (13) is typically reacted with an amine of the formula R$^5$R$^6$NH; wherein R$^5$ and R$^6$ are as defined in any one of Embodiments 1.1 to 1.52, at a temperature between about 0° C. to about 110° C. in a solvent such as toluene in combination with a reagent such as Me$_3$Al, optionally in the presence of a tertiary base such as TEA or DIPEA. It will be well known to the skilled person that other suitable conditions exist to effect the same transformation, such as reaction in the presence of $^i$PrMgCl in a suitable solvent, or direct heating, optionally in the presence of a suitable solvent.

Compounds of formula (13) can be prepared by the reaction shown in Scheme 7 below:

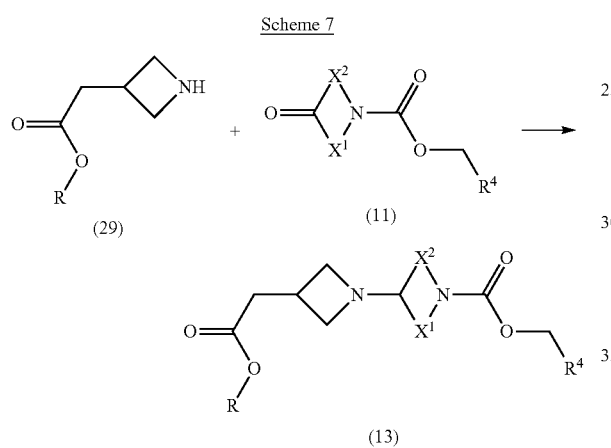

Thus, an amine of formula (29), wherein R represents a suitable group such as methyl- or ethyl-, is reacted with under reductive amination conditions with a compound of formula (11), wherein R$^4$, X$^1$, and X$^2$ are as defined in any one of Embodiments 1.1 to 1.52, to form a compound of formula (13). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or NaCNBH$_3$ in combination with ZnCl$_2$ in a solvent such as MeOH, or STAB in a solvent such as DCM or DCE containing an acid such as AcOH or TFA in combination with Ti(O$^i$Pr)$_4$. Optionally, amine (29) may be present in the reaction as an acid salt such as an HCl, HBr or a TFA salt, optionally in the presence of a tertiary base such as TEA or DI PEA.

In process variant (D), the compound of formula (14) is typically reacted with an amine of the formula R$^5$R$^6$NH, wherein R$^5$ and R$^6$ are as defined in any one of Embodiments 1.1 to 1.52, using suitable amide coupling conditions. It will be well known to the skilled person that many suitable conditions exist in the art to effect formation of an amide from the compound of formula (14) and an amine of the formula R$^5$R$^6$NH, for example using a reagent such as DIC, EDC, PyBOP, HATU, COMU or T3P, optionally in the presence of a tertiary base such as TEA or DI PEA, optionally in the presence of HOBt, in a solvent such as DCM, THF or DMF, at a temperature between about 0° C. to about 100° C. Alternatively, the compound of formula (14) can be reacted with an amine of the formula R$^5$R$^6$NH using the sequence of reactions shown in Scheme 8 below:

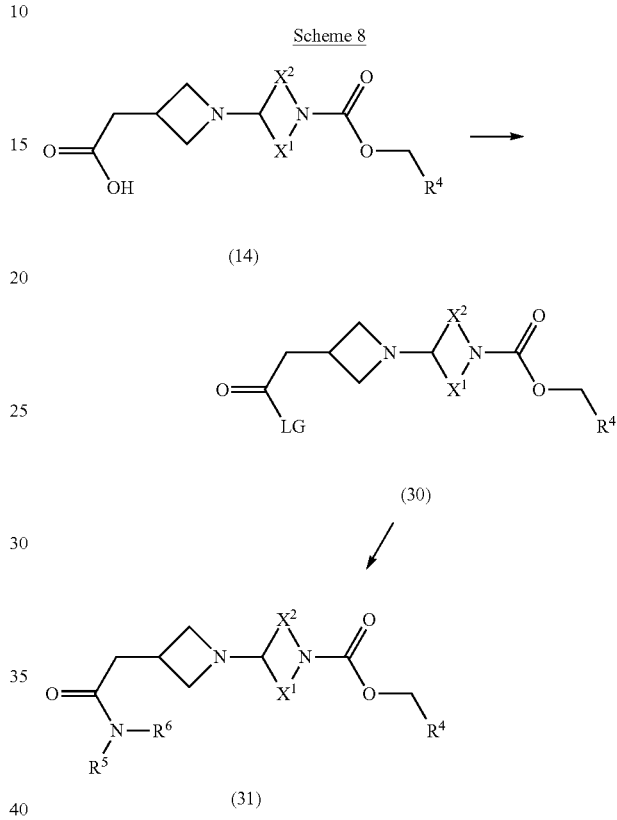

Thus, a compound of formula (14), wherein R$^4$, X$^1$, and X$^2$ are as defined in any one of Embodiments 1.1 to 1.52, can be reacted under conditions suitable to effect formation of intermediate (30), wherein LG represents a suitable leaving group such as Cl, 1-imidazole, or RO(C=O)O (wherein R represents a group such as ethyl- or isobutyl-). Typically, such conditions are reaction with a reagent such as oxalyl chloride or thionyl chloride (LG=Cl), CDI (LG=1-imidazole) or ethyl- or isobutyl-chloroformate (LG=RO(C=O)O), optionally in the presence of a tertiary base such as TEA or DIPEA, optionally in the presence of a catalyst such as DMF, in a suitable solvent such as DCM, THF or DMF. Once formed, the intermediate (30) is reacted with an amine of the formula R$^5$R$^6$NH, wherein R$^5$ and R$^6$ are as defined in any one of Embodiments 1.1 to 1.52, under conditions suitable to effect formation of a compound of formula (31). Typically, such conditions are reaction at a temperature between about 0° C. to about 100° C. in a solvent such as DCM, THF or DMF, optionally in the presence of a tertiary base such as TEA or DIPEA.

Compounds of formula (14) can be prepared by the reaction shown in Scheme 9 below:

Scheme 9

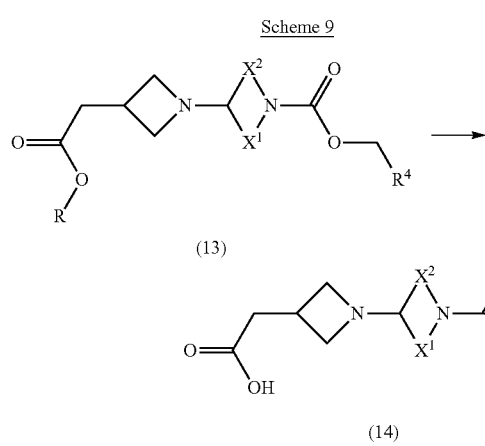

Thus, a compound of formula (13), wherein R represents a suitable group such as methyl- or ethyl- and $R^4$, $X^1$ and $X^2$ are as defined in any one of Embodiments 1.1 to 1.52, can be reacted under conditions suitable to effect hydrolysis of the ester to form a compound of formula (14). For example, reaction with a reagent such as LiOH, NaOH or KOH in a solvent such as THF, MeOH, EtOH, $H_2O$ or a combination of two or more of the aforementioned solvents, at a temperature between about 0° C. to about 100° C.

In process variant (E), the compound of formula (15) is reacted with an amine of the formula $R^5R^6NH$, wherein $R^5$ and $R^6$ are as defined in any one of Embodiments 1.1 to 1.52 under conditions suitable to effect the formation of a carbamate. Typically, such conditions might be as illustrated in Scheme 10 below:

Scheme 10

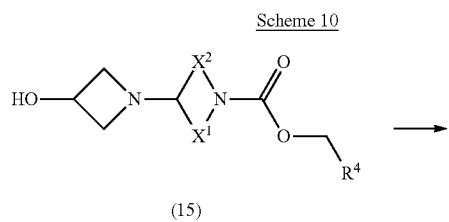

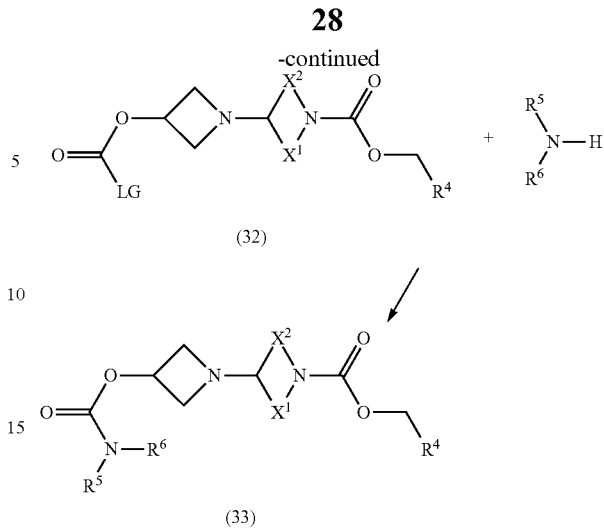

Thus, the compound of formula (15), wherein $R^4$, $X^1$ and $X^2$ are as defined in any one of Embodiments 1.1 to 1.52, is first reacted under conditions suitable to effect formation of intermediate (32), wherein LG represents a suitable leaving group such as Cl, 1-imidazole, or 4-nitrophenol. Typically, such conditions are reaction with a reagent such as phosgene or triphosgene (LG=Cl), CDI (LG=1-imidazole) or 4-nitrophenyl-chloroformate (LG=4-nitrophenol), optionally in the presence of a tertiary base such as TEA or DIPEA, in a suitable solvent such as DCM, THF or DMF. Once formed, the intermediate (32), is reacted with an amine of the formula $R^5R^6NH$, wherein $R^5$ and $R^6$ are as defined in any one of Embodiments 1.1 to 1.52, under conditions suitable to effect formation of dicarbamate (33). Typically, such conditions are reaction at a temperature between about 0° C. to about 100° C. in a solvent such as DCM, THF or DMF, optionally in the presence of a tertiary base such as TEA or DI PEA.

Compounds of formula (15) can be prepared using the sequence of reactions shown in Scheme 11 below:

Scheme 11

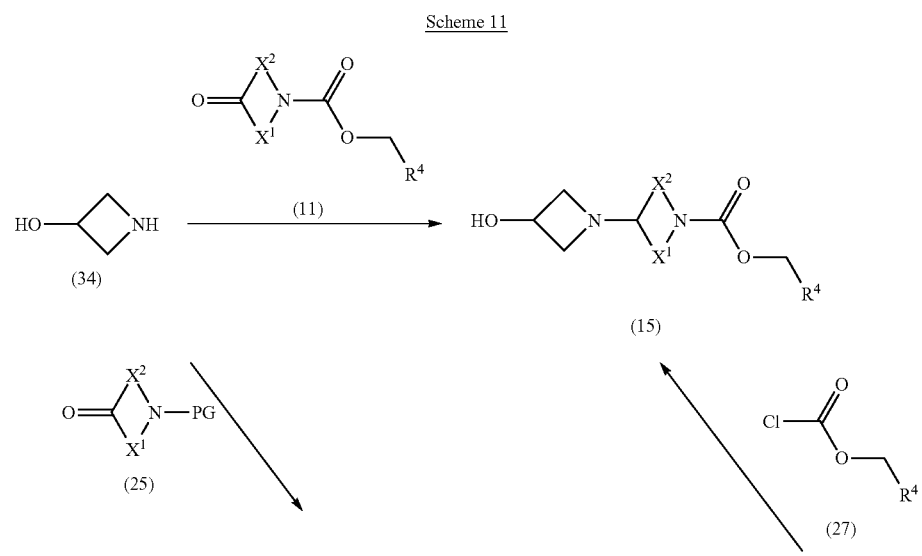

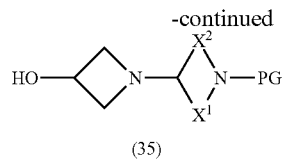 (35) 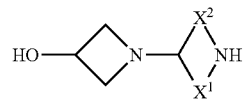 (36)

Thus, azetidin-3-ol (34) can be reacted with a ketone of formula (11), wherein $R^4$, $X^1$, and $X^2$ are as defined in any one of Embodiments 1.1 to 1.52, under reductive amination conditions to form a compound of formula (15). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or $NaCNBH_3$ in combination with $ZnCl_2$ in a solvent such as MeOH, or STAB in a solvent such as DCM or DCE containing an acid such as AcOH or TFA in combination with $Ti(O^iPr)_4$. Optionally, azetidin-3-ol (34) may be present in the reaction as an acid salt such as an HCl, HBr or a TFA salt, optionally in the presence of a tertiary base such as TEA or DIPEA. Alternatively, azetidin-3-ol (34) can be reacted with a ketone of formula (25), wherein $X^1$ and $X^2$ are as defined in any one of Embodiments 1.1 to 1.52 and PG represents a suitable protecting group such as BOC or CBZ, under reductive amination conditions to form a protected amino alcohol of formula (35). The reductive amination reaction can be typically carried out as described above. Once formed, the protecting group PG can be removed from the protected amino alcohol of formula (35) to form an amino alcohol of formula (36). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ then suitable conditions to effect its removal might be reaction with $H_2$ in the presence of a Pd/C catalyst in a solvent such as EtOH at a temperature of about 20° C. to about 80° C. Once formed, the amino alcohol of formula (36) can be reacted with chloroformate (27), wherein $R^4$ is as defined in any one of Embodiments 1.1 to 1.52, under suitable conditions to form a compound of formula (15). Typically, such conditions are reaction at a temperature between about 0° C. to about 50° C. in a solvent such as DCM, THF or DMF, optionally in the presence of a tertiary base such as TEA or DIPEA.

In process variant (F), one compound of the formula (1) can be converted into another compound of the formula (1) by methods well known to the skilled person. Examples of synthetic procedures for converting one functional group into another functional group are set out in standard texts such as *March's Advanced Organic Chemistry; Reactions, Mechanisms, and Structure*, 7th Edition, Michael B. Smith, John Wiley, 2013, (ISBN: 978-0-470-46259-1), *Organic Syntheses*, Online Edition, www.orgsyn.org, (ISSN 2333-3553) and *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis*, Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.52 together with at least one pharmaceutically acceptable excipient.

In one embodiment (Embodiment 4.2), the composition is a tablet composition.

In another embodiment (Embodiment 4.3), the composition is a capsule composition. The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient.

Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 8-1

The compounds of Examples 1-1 to 8-1 shown in Table 1 below have been prepared. Their NMR and LCMS properties and the methods used to prepare them are set out in Table 3. The starting materials for each of the Examples are listed in Table 2.

TABLE 1

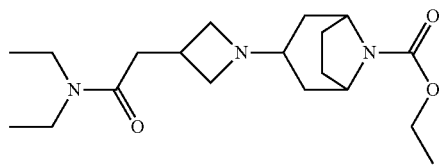 [SMILES: CCOC(=O)N1C2CCC1CC(N1CC(CC(=O)N(CC)CC)C1)C2]

Example 1-1

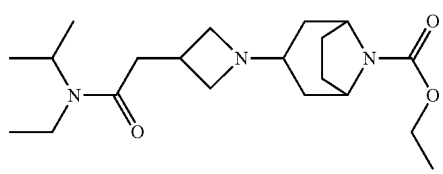

Example 1-2

TABLE 1-continued
| | |
|---|---|
| 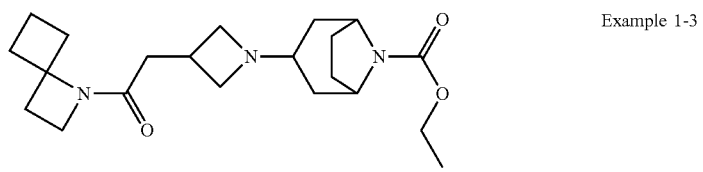 | Example 1-3 |
| 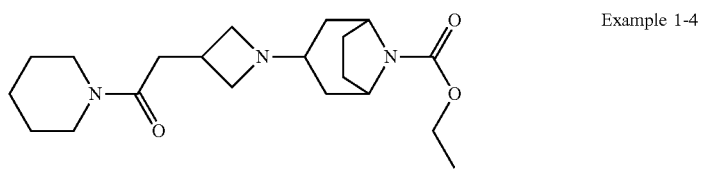 | Example 1-4 |
| 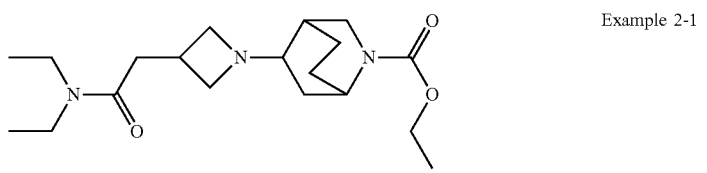 | Example 2-1 |
| 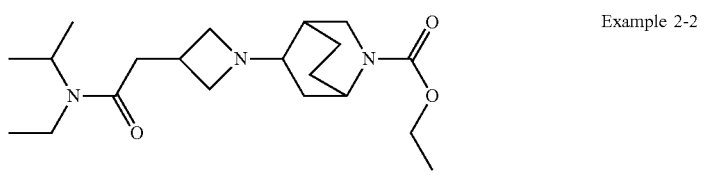 | Example 2-2 |
| 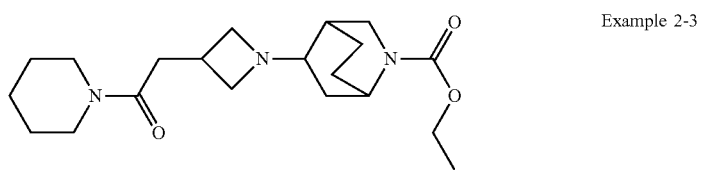 | Example 2-3 |
| 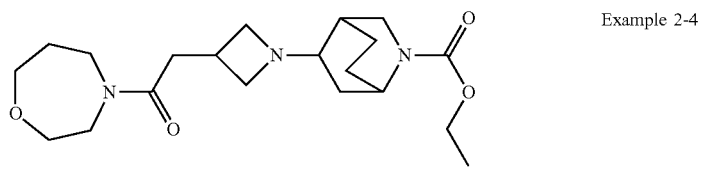 | Example 2-4 |
| 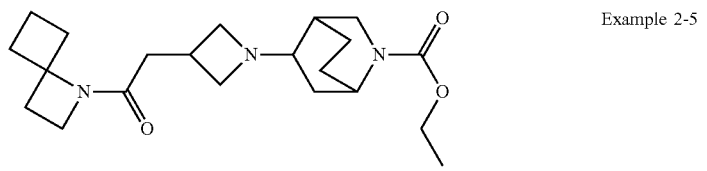 | Example 2-5 |
| 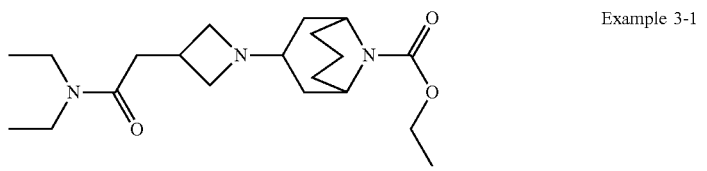 | Example 3-1 |
| 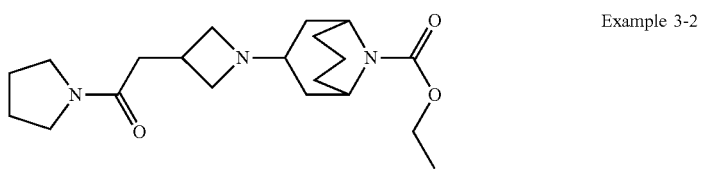 | Example 3-2 |

TABLE 1-continued
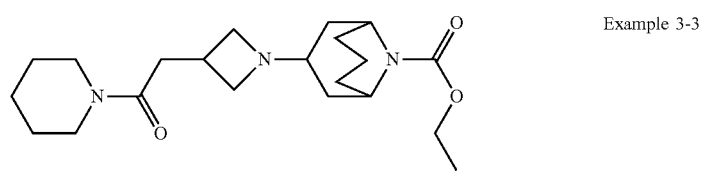
Example 3-3
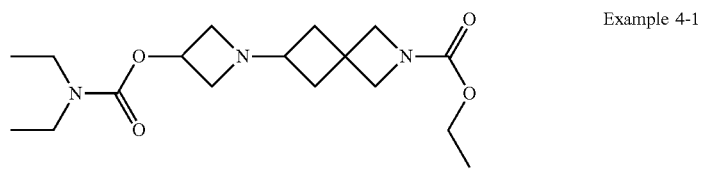
Example 4-1
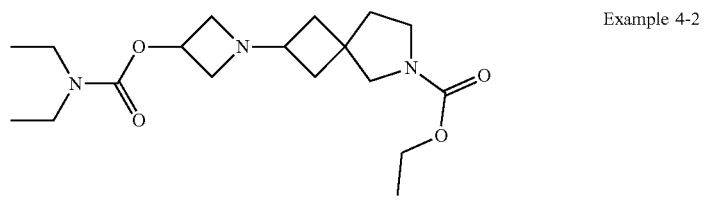
Example 4-2
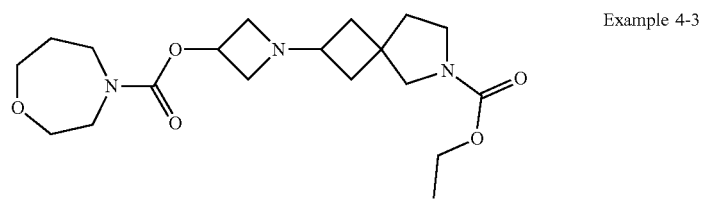
Example 4-3
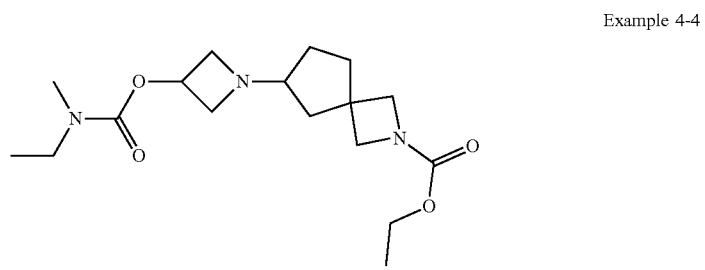
Example 4-4
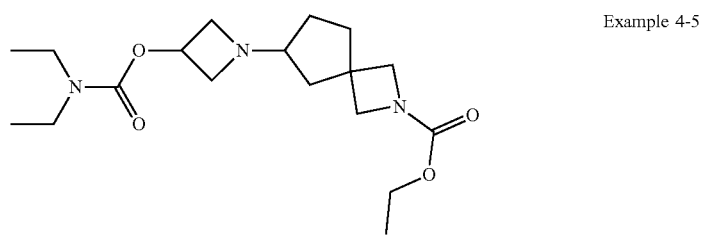
Example 4-5
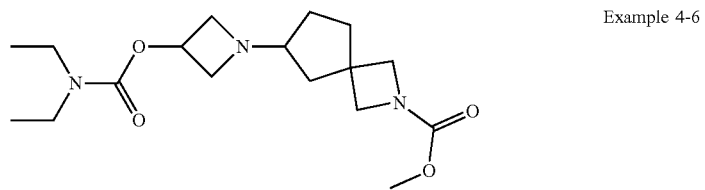
Example 4-6

TABLE 1-continued
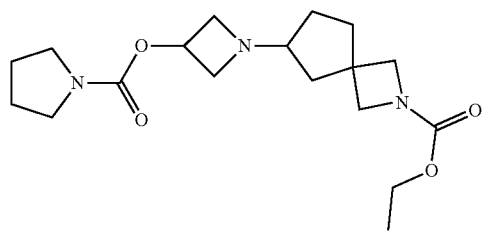 [SMILES: CCOC(=O)N1CC2(CCC(N3CC(OC(=O)N4CCCC4)C3)C2)C1] Example 4-7
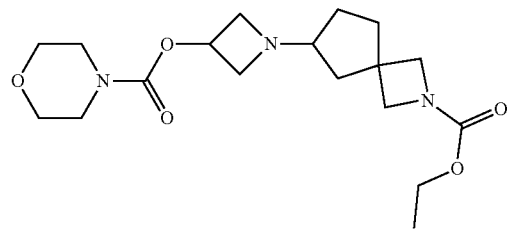 [SMILES: CCOC(=O)N1CC2(CCC(N3CC(OC(=O)N4CCOCC4)C3)C2)C1] Example 4-8
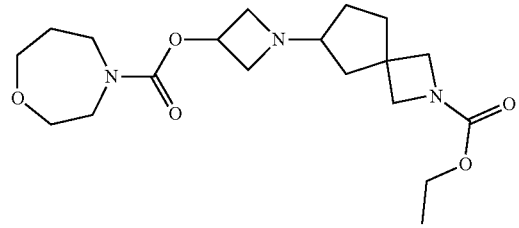 [SMILES: CCOC(=O)N1CC2(CCC(N3CC(OC(=O)N4CCCOCC4)C3)C2)C1] Example 4-9
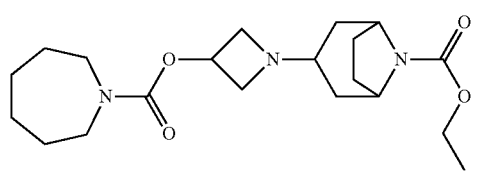 [SMILES: CCOC(=O)N1C2CCC1CC(N1CC(OC(=O)N3CCCCCC3)C1)C2] Example 5-1
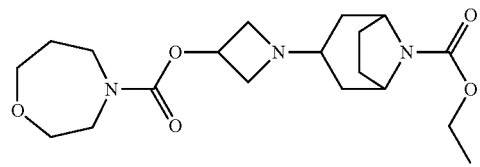 [SMILES: CCOC(=O)N1C2CCC1CC(N1CC(OC(=O)N3CCCOCC3)C1)C2] Example 5-2
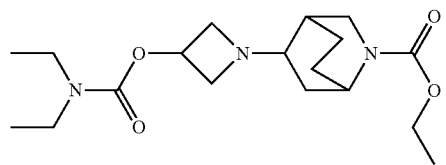 [SMILES: CCOC(=O)N1CC2CCC1CC2N1CC(OC(=O)N(CC)CC)C1] Example 6-1
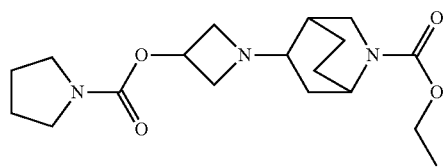 [SMILES: CCOC(=O)N1CC2CCC1CC2N1CC(OC(=O)N2CCCC2)C1] Example 6-2
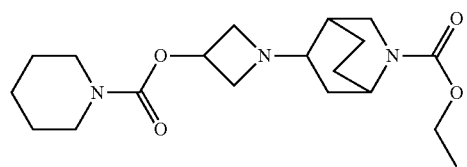 Example 6-3

TABLE 1-continued

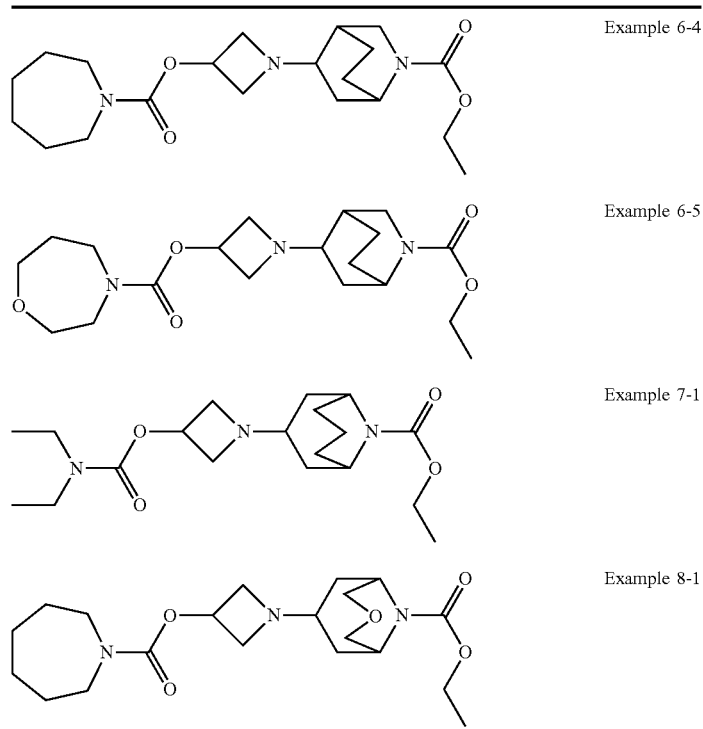

| | |
|---|---|
| | Example 6-4 |
| | Example 6-5 |
| | Example 7-1 |
| | Example 8-1 |

General Procedures

Where no preparative routes are included, the relevant intermediate is commercially available. Commercial reagents were utilized without further purification. Room temperature (rt) refers to approximately 20-27° C. ¹H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks.

Chromatography refers to column chromatography performed using 60-120 mesh silica gel and executed under nitrogen pressure (flash chromatography) conditions. TLC for monitoring reactions refers to TLC run using the specified mobile phase and the Silica gel F254 as a stationary phase from Merck. Microwave-mediated reactions were performed in Biotage Initiator or CEM Discover microwave reactors.

LCMS Analysis

LCMS analysis of compounds was performed under electrospray conditions using the instruments and methods given in the tables below.

LCMS data in the experimental section and Tables 2 and 3 are given in the format: (Instrument system, Method): Mass ion, retention time, UV detection wavelength.

| System ID | Instrument Name | LC Detector | Mass Detector |
|---|---|---|---|
| 1 | Waters 2695 | Photo Diode Array | ZQ-2000 Detector |
| 2 | Waters Acquity H Class | Photo Diode Array | SQ Detector |
| 3 | Shimadzu Nexera | Photo Diode Array | LCMS-2020 |
| 4 | Agilent 1290 RRLC with Agilent 6120 Mass detector | Photo Diode Array | Agilent 6120 |

| Method Name | Solvent System | Column used | Gradient | UV Range | Mass Range | Column Temp. ° C. | Flow Rate ml/min |
|---|---|---|---|---|---|---|---|
| A | (A) 5 mM ammonium acetate + 0.1% formic acid in water (B) 0.1% formic acid in acetonitrile | BEH C18 2.1 × 50 mm, 1.7 µm or equivalent | 95:5 at 0.01 min up to 0.40 min, 65:35 at 0.80 min, 45:55 at 1.20 min, 0:100 at 2.50 min up to 3.30 min, 95:5 at 3.31 min up to 4.00 min | 200-400 nm | 100-1200 amu | Ambient | 0.55 |
| B | (A) 20 mM ammonium acetate in water (B) methanol | X-Bridge C18 4.6 × 150 mm, 5 µm or equivalent | 90:10 at 0.01 min, 10:90 at 5.00 min, 0.100 at 7.00 min up to 11.00 min, 90:10 at 11:01 min up to 12.00 min | 200-400 nm | 60-1000 amu | Ambient | 1.00 |

| Method Name | Solvent System | Column used | Gradient | UV Range | Mass Range | Column Temp. °C. | Flow Rate ml/min |
|---|---|---|---|---|---|---|---|
| C | (A) 0.1% ammonia in water (B) 0.1% ammonia in acetonitril | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |
| D | (A) 5 mM ammonium acetate + 0.1% formic acid in water (B) 0.1% formic acid in acetonitril | BEH C18 2.1 × 50 mm, 1.7 μm or equivalent | 95:5 at 0.01 min up to 0.40 min, 60:40 at 0.60 min, 40:60 at 1.20 min, 0:100 at 2.30 min up to 3.00 min, 95:5 at 3.01 min up to 3.50 min | 200-400 nm | 100-1200 amu | Ambient | 0.55 |
| E | (A) 5 mM ammonium bicarbonate in water (B) acetonitrile | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |

Compound Purification

Final purification of compounds was performed by preparative reversed phase HPLC, chiral HPLC or chiral SFC using the instruments and methods detailed below where data is given in the following format: Purification technique: [phase (column description, column length×internal diameter, particle size), solvent flow-rate, gradient—given as % of mobile phase B in mobile phase A (over time), mobile phase (A), mobile phase (B)].

Preparative HPLC purification:
Shimadzu LC-20AP and UV detector
Chiral HPLC purification:
Shimadzu LC-20AP binary system with SPD-20A UV detector
Chiral SFC purification:
Waters SFC 200

Purification Method A
Prep HPLC: [Reversed Phase (X-BRIDGE C-18, 250×19 mm, 5 μm), 5 mL per min, gradient 40-65% (over 22 min), 65% (over 8 min), 100% (over 4 min), then 100-40% (over 6 min), mobile phase (A): 5 mM ammonium bicarbonate in water, (B) 100% acetonitrile]

Purification Method B
Prep HPLC: [Reversed phase (X-BRIDGE C-8, 250×19 mm, 5 μm), 16 mL per min, gradient 20-60% (over 30 min), 100% (over 3 min), then 100-20% (over 2 min), mobile phase (A): 5 mM ammonium bicarbonate+0.05% ammonia in water, (B) 100% acetonitrile]

Purification Method C
Prep HPLC: [Reversed Phase (X-BRIDGE C-8, 250×19 mm, 5 μm), 15 mL per min, gradient 30-55% (over 22 min), 100% (over 2 min), then 100-30% (over 3 min), mobile phase (A): 5 mM ammonium bicarbonate+0.1% ammonia in water, (B) 100% acetonitrile]

Purification Method D
Prep HPLC: [Reversed Phase (X-BRIDGE C-18, 250×19 mm, 5 μm), 15 mL per min, gradient 35-45% (over 25 min), 100% (over 5 min), then 100-35% (over 1 min), mobile phase (A): 5 mM ammonium bicarbonate in water, (B) 100% acetonitrile]

Purification Method E
Prep HPLC: [Reversed Phase (X SELECT PHENYL HEXYL, 250×19 mm, 5 μm), 9 mL per min, gradient 15-20% (over 10 min), 20-25% (over 70 min), 100% (over 4 min), then 100-15% (over 6 min), mobile phase (A): 5 mM ammonium bicarbonate in water, (B) 100% acetonitrile]

Purification Method F
Prep HPLC: [Reversed Phase (X-BRIDGE C-8, 250×19 mm, 5 μm), 15 mL per min, gradient 28% (over 24 min), 100% (over 3 min), then 100-28% (over 4 min), mobile (A): 5 mM ammonium bicarbonate in water, (B) 100% acetonitrile]

Purification Method G
Prep HPLC: [Reversed phase (X-BRIDGE C-18, 250×19 mm, 5 μm), 17 mL per min, gradient 20% (over 75 min), 100% (over 5 min), then 100-20% (over 5 min), mobile phase (A): 5 mM ammonium bicarbonate in water, (B) 100% acetonitrile]

Purification Method H
Prep HPLC: [Reversed Phase (X SELECT PHENYL HEXYL, 250×19 mm, 5 μm), 15 mL per min, gradient 0-30% (over 25 min), 100% (over 2 min), then 100-0% (over 3 min), mobile phase (A): 5 mM ammonium bicarbonate+0.1% ammonia in water, (B) 100% acetonitrile]

Purification Method I
Prep HPLC: [Reversed Phase (X-BRIDGE C-8, 250×19 mm, 5 μm), 15 mL per min, gradient 23-27% (over 20 min), 27% (over 25 min), 27-100% (over 15 min), 100% (over 1 min), then 100-23% (over 2 min), mobile phase (A): 5 mM ammonium bicarbonate+0.1% ammonia in water, (B) 100% acetonitrile]

Purification Method J
Prep HPLC: [Reversed phase (X-BRIDGE C-8, 250×19 mm, 5 μm), 17 mL per min, gradient 20-55% (over 16 min), 100% (over 3 min), then 100-20% (over 3 min), mobile phase (A): 5 mM ammonium bicarbonate+0.05% ammonia in water, (B) 100% acetonitrile]

Purification Method K
Prep HPLC: [Reversed phase (X-BRIDGE C-8, 250×19 mm, 5 μm), 17 mL per min, gradient 20-30% (over 40 min), 100% (over 4 min), then 100-20% (over 6 min), mobile phase (A): 5 mM ammonium bicarbonate+0.05% ammonia in water, (B) 100% acetonitrile]

Purification Method L
Prep HPLC: [Reversed phase (X-BRIDGE C-8, 250×19 mm, 5 μm), 17 mL per min, gradient 23-33% (over 20 min), 33% (over 15 min), 100% (over 4 min), then 100-23% (over 4 min), mobile phase (A): 5 mM ammonium bicarbonate+0.05% ammonia in water, (B) 100% acetonitrile]

Purification Method M
Prep HPLC: [Reversed Phase (X-BRIDGE C-18, 250×19 mm, 5 μm), 17 mL per min, gradient 28-34% (over 25 min), 100% (over 2 min), then 100-28% (over 3 min), mobile phase (A): 5 mM ammonium bicarbonate+0.05% ammonia in water, (B) 100% acetonitrile]

Purification Method N
Prep HPLC: [Reversed Phase (X-BRIDGE C-18, 250×19 mm, 5 μm), 16 mL per min, gradient 10-26% (over 20 min), 26-29% (over 33 min), 29% (over 23 min), 100% (over 3 min), then 100-10% (over 6 min), mobile phase (A): 5 mM ammonium bicarbonate+0.1% ammonia in water, (B) 100% acetonitrile]

Purification Method O

Prep HPLC: [Reversed Phase (X-BRIDGE C-8, 250×19 mm, 5 μm), 15 mL per min, gradient 10-50% (over 28 min), 50% (over 4 min), 100% (over 2 min), then 100-10% (over 3 min), mobile phase (A): 5 mM ammonium bicarbonate+0.1% ammonia in water, (B):acetonitrile:methanol (50:50)]

Purification Method P

Prep HPLC: [Reversed Phase (X-BRIDGE C-18, 250×19 mm, 5 μm), 15 mL per min, gradient 15-30% (over 30 min), 30% (over 5 min), 100% (over 2 min), then 100-15% (over 3 min), mobile phase (A): 5 mM ammonium acetate in water, (B) 100% acetonitrile]

Purification Method Q

SFC: [(CHIRALCEL OX—H, 250×21 mm, 5 μm), 70 mL per min, Isocratic (A:B) (80:20) (over 10 min), mobile phase (A): 100% liquid $CO_2$, (B): 0.1% diethylamine in isopropanol]

Purification Method R

Prep HPLC: [Reversed phase (X-BRIDGE C-8, 250×19 mm, 5 μm), 17 mL per min, gradient 0% (over 3 min), 0-50% (over 30 min), 100% (over 2 min), then 100-0% (over 2 min), mobile phase (A): 5 mM ammonium bicarbonate+0.1% ammonia in water, (B) 100% acetonitrile]

Purification Method S

SFC: [(CHIRALCEL OX—H, 250×21 mm, 5 μm), 70 mL per min, Isocratic (A:B) (85:15) (over 10 min), mobile phase (A): 100% liquid $CO_2$, (B): 0.1% diethylamine in methanol]

Purification Method T

Prep HPLC: [Reversed Phase (X-BRIDGE C-8, 250×19 mm, 5 μm), 15 mL per min, gradient 10-40% (over 18 min), 40% (over 5 min), 100% (over 2 min), then 100-10% (over 3 min), mobile phase (A): 10 mM ammonium acetate in water, (B) 100% acetonitrile]

Purification Method U

Prep HPLC: [Reversed Phase (X SELECT PHENYL HEXYL, 250×19 mm, 5 μm), 15 mL per min, gradient 0-60% (over 25 min), 100% (over 2 min), then 100-0% (over 3 min), mobile phase (A): 5 mM ammonium bicarbonate+0.1% ammonia in water, (B) 100% acetonitrile]

Purification Method V

Chiral HPLC: [Normal Phase (CHIRALCEL OX—H, 250×21 mm, 5 μm), 18 mL per min, Isocratic (A:B) (60:40) (over 25 min), mobile phase (A): 0.1% diethylamine in hexane, (B): 0.1% diethylamine in isopropanol]

Purification Method W

Prep HPLC: [Reversed phase (X-BRIDGE C-8, 250×19 mm, 5 μm), 16 mL per min, gradient 20-30% (over 18 min), 30% (over 4 min), 100% (over 2 min), then 100-20% (over 3 min), mobile phase (A): 5 mM ammonium bicarbonate+0.1% ammonia in water, (B) 100% acetonitrile]

Purification Method X

SFC: [(CHIRALCEL OX—H, 250×21 mm, 5 μm), 70 mL per min, Isocratic (A:B) (85:15) (over 14 min), mobile phase (A): 100% liquid $CO_2$, (B): 0.1% diethylamine in isopropanol]

Purification Method Y

Prep HPLC: [Reversed Phase (PHENOMENEX LUNA C-18, 250×21.2 mm, 5 μm), 16 mL per min, gradient 15-45% (over 25 min), 100% (over 2 min), then 100-15% (over 3 min), mobile phase (A): 10 mM ammonium acetate in water, (B) 100% acetonitrile]

Purification Method Z

Prep HPLC: [Reversed Phase (X SELECT PHENYL HEXYL, 250×19 mm, 5 μm), 16 mL per min, gradient 30-55% (over 30 min), 55% (over 3 min), 100% (over 2 min), then 100-30% (over 2 min), mobile phase (A): 5 mM ammonium bicarbonate+0.1% ammonia in water, (B) 100% acetonitrile]

Purification Method AA

Prep HPLC: [Reversed Phase (X-BRIDGE C-18, 250×19 mm, 5 μm), 15 mL per min, gradient 15-58% (over 23 min), 100% (over 2 min), then 100-15% (over 2 min), mobile phase (A): 5 mM ammonium bicarbonate+0.1% ammonia in water, (B) 100% acetonitrile]

Purification Method AB

Prep HPLC: [Reversed phase (X-BRIDGE C-8, 250×19 mm, 5 μm), 18 mL per min, gradient 25-56% (over 20 min), 100% (over 2 min), then 100-25% (over 3 min), mobile phase (A): 5 mM ammonium bicarbonate+0.05% ammonia in water, (B) 100% acetonitrile]

Purification Method AC

Prep HPLC: [Reversed phase (X-BRIDGE C-8, 250×19 mm, 5 μm), 16 mL per min, gradient 10-45% (over 16 min), 45% (over 6 min), 100% (over 2 min), then 100-10% (over 4 min), mobile phase (A): 5 mM ammonium bicarbonate in water, (B) 100% acetonitrile]

Purification Method AD

Prep HPLC: [Reversed Phase (X-BRIDGE C-18, 250×19 mm, 5 μm), 16 mL per min, gradient 30-42% (over 18 min), 42% (over 10 min), 100% (over 2 min), then 100-30% (over 3 min), mobile phase (A): 5 mM ammonium bicarbonate+0.05% ammonia in water, (B) 100% acetonitrile]

Purification Method AE

Prep HPLC: [Reversed Phase (X SELECT PHENYL HEXYL, 250×19 mm, 5 μm), 15 mL per min, gradient 5-25% (over 20 min), 100% (over 2 min), then 100-5% (over 3 min), mobile phase (A): 0.1% formic acid in water, (B) 100% acetonitrile]

Purification Method AF

Prep HPLC: [Reversed Phase (X-BRIDGE C-18, 250×19 mm, 5 μm), 13 mL per min, gradient 10-50% (over 22 min), 100% (over 3 min), then 100-10% (over 5 min), mobile phase (A): 10 mM ammonium acetate in water, (B) 100% acetonitrile]

Purification Method AG

Prep HPLC: [Reversed phase (X-BRIDGE C-8, 250×19 mm, 5 μm), 16 mL per min, gradient 32% (over 50 min), 100% (over 3 min), then 100-32% (over 3 min), mobile phase (A): 5 mM ammonium bicarbonate+0.05% ammonia in water, (B) 100% acetonitrile]

Purification Method AH

Prep HPLC: [Reversed Phase (SUNFIRE C-18, 250×19 mm, 5 μm), 13 mL per min, gradient 0-17% (over 25 min), 17% (over 7 min), 100% (over 2 min), then 100-0% (over 3 min), mobile phase (A): 0.1% formic acid in water, (B) 100% acetonitrile]

Abbreviations

DCM=dichloromethane
ES(I)=electro spray ionisation
EtOAc=ethyl acetate
h=hour(s)
$H_2O$=water
HCl=hydrogen chloride, hydrochloric acid
HPLC=high performance liquid chromatography
IPA=propan-2-ol
LC=liquid chromatography MeOH=methanol
min(s)=minute(s)
MS=mass spectrometry
nm=nanometre(s)
NMR=nuclear magnetic resonance
SFC=supercritical fluid chromatography
TEA=triethylamine
TFA=trifluoroacetic acid
TLC=thin layer chromatography Prefixes n-, s-, i-, t- and tert- have their usual meanings: normal, secondary, iso, and tertiary.

Synthesis of Intermediates:

Route 1

Typical Procedure for the Preparation of Esters, as Exemplified by the Preparation of Intermediate 3, ethyl-3-(3-(2-methoxy-2-oxoethyl)azetidin-1-yl)-8-azabicyclo[3.2.1]octane-8-carboxylate

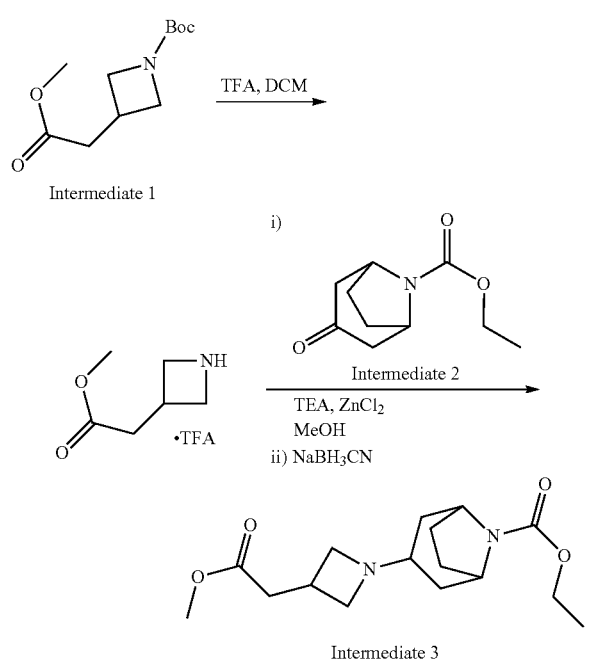

Intermediate 3 tert-Butyl 3-(2-methoxy-2-oxoethyl)azetidine-1-carboxylate (Intermediate 1) (150 mg, 0.66 mmol) was dissolved in DCM (5 mL) and cooled to 0° C. To this was added TFA (1 mL) drop-wise and the resulting reaction mixture was stirred at room temperature for 5 h. Solvents were removed in vacuo and the residue was purified by trituration with diethyl ether (3×1 mL) to give methyl 2-(azetidin-3-yl)acetate trifluoroacetate (110 mg, >100%) as a gum.

LCMS (System 1, Method C): m/z 130 (M+H)+ (ESI+ve), at 2.37 min, 202 nm.

Methyl 2-(azetidin-3-yl)acetate trifluoroacetate (200 mg, 1.55 mmol), ethyl 3-oxo-8-azabicyclo[3.2.1]octane-8-carboxylate (Intermediate 2) (305 mg, 1.55 mmol), TEA (0.7 mL, 4.65 mmol) and ZnCl$_2$ (21 mg, 0.16 mmol) were dissolved in MeOH (10 mL) and the reaction mixture was stirred at 65° C. for 8 h. The reaction was then cooled to 0° C. and to this was then added NaBH$_3$CN (293 mg, 4.65 mmol) portion wise. The resulting reaction mixture was stirred at 60° C. for 30 h. The solvents were removed in vacuo and the residue was partitioned between H$_2$O (100 mL) and EtOAc (80 mL), extracting the aqueous layer further with EtOAc (2×80 mL). The combined organic phases were dried (Na$_2$SO$_4$), concentrated in vacuo and the residue was purified by column chromatography (normal phase neutral activated alumina, 50% to 60% EtOAc in hexane) to give ethyl-3-(3-(2-methoxy-2-oxoethyl)azetidin-1-yl)-8-azabicyclo[3.2.1]octane-8-carboxylate (Intermediate 3) (140 mg, 29%) as a gum.

The data for Intermediate 3 are in Table 2.

Route 2

Typical Procedure for the Preparation of Ketones, as Exemplified by the Preparation of Intermediate 8, ethyl 5-oxo-2-azabicyclo[2.2.2]octane-2-carboxylate

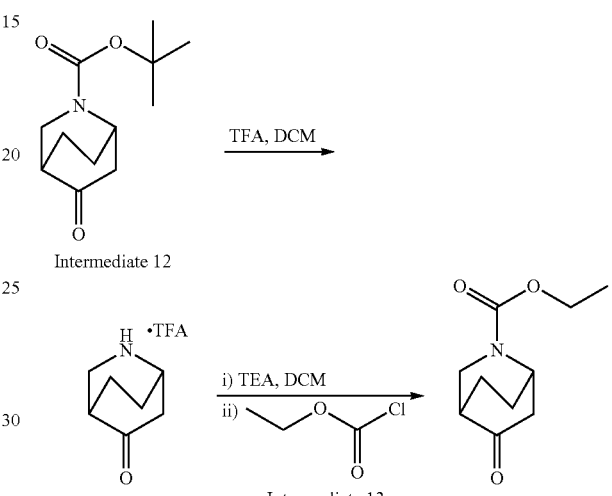

A solution of tert-butyl 5-oxo-2-azabicyclo[2.2.2]octane-2-carboxylate (Intermediate 12) (550 mg, 2.44 mmol) and TFA (2.50 mL) in DCM (5 mL) was stirred under nitrogen at room temperature for 3 h. The reaction mixture was concentrated in vacuo and the residue co-evaporated from diethyl ether (2×5 mL) and toluene (2×10 mL) to give 2-azabicyclo[2.2.2]octan-5-one trifluoroacetate (280 mg, 92%) as a gum.

LCMS (System 1, Method C): m/z 126 (M+H)+ (ESI+ve), at 1.41 min, 202 nm.

A solution of 2-azabicyclo[2.2.2]octan-5-one trifluoroacetate (275 mg, 2.20 mmol) and TEA (0.92 mL, 6.59 mmol) in DCM (10 mL) was stirred at 0° C. under nitrogen for 10 min. To this was then added ethyl carbonochloridate (Intermediate 13) (356 mg, 3.30 mmol) drop-wise at 0° C. to 10° C. and the reaction was then allowed to warm to room temperature and stirred for 2 h. The reaction mixture was partitioned between H$_2$O (20 mL) and EtOAc (15 mL) and the aqueous layer was further extracted with EtOAc (2×15 mL). The combined organic phases were dried (Na$_2$SO$_4$), concentrated in vacuo and the residue was purified by column chromatography (normal phase silica, 0% to 2% MeOH in DCM) to give ethyl 5-oxo-2-azabicyclo[2.2.2] octane-2-carboxylate (Intermediate 8) (308 mg, 71%) as a gum.

The data for Intermediate 8 are in Table 2.

Route 3

Typical Procedure for the Preparation of Carbamates, as Exemplified by the Preparation of Intermediate 20, azetidin-3-yl diethylcarbamate trifluoroacetate

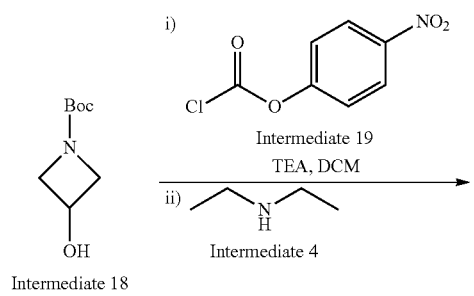

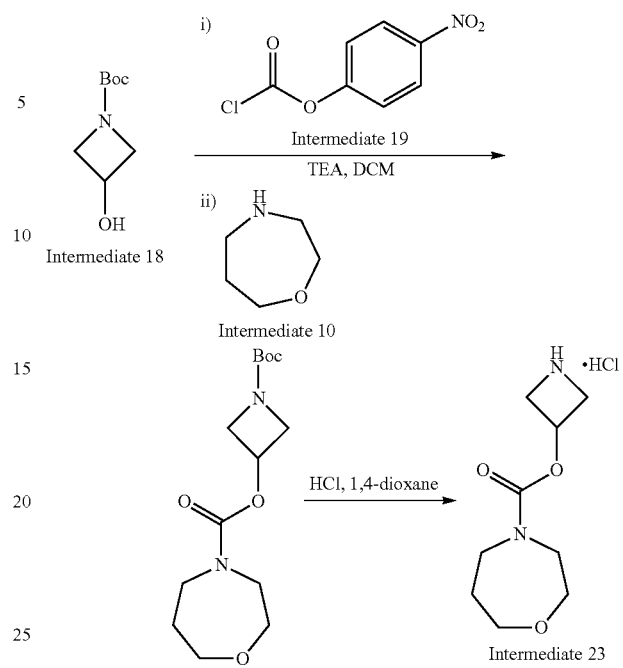

To a stirred solution of tert-butyl 3-hydroxyazetidine-1-carboxylate (Intermediate 18) (3.0 g, 17.3 mmol) in DCM (90 mL) was added TEA (12.5 mL, 86.7 mmol). The reaction was stirred at room temperature for 15 min and then cooled to 0° C. To this was then added portion wise 4-nitrophenyl carbonochloridate (Intermediate 19) (12.2 g, 60.7 mmol) and the reaction was then allowed to warm to room temperature and stirred for 4 h. To this was then added diethylamine (Intermediate 4) (4.4 mL, 60.7 mmol) and the reaction was stirred at room temperature for 16 h. The reaction mixture was partitioned between H$_2$O (30 mL) and DCM (50 mL). The organic phases were concentrated in vacuo and the residue was purified by column chromatography (neutral alumina, EtOAc in hexane) to give tert-butyl 3-((diethylcarbamoyl)oxy)azetidine-1-carboxylate (3.6 g, 74%) as a gum.

LCMS (System 2, Method D): m/z 273 (M+H)$^+$ (ESI+ve), at 1.99 min, 202 nm.

To the stirred solution of tert-butyl 3-((diethylcarbamoyl)oxy)azetidine-1-carboxylate (1.0 g, 3.7 mmol) in DCM (15 mL) at 0° C. was added TFA (5 mL) drop-wise. The reaction was warmed to room temperature and stirred for 3 h. The reaction mixture was concentrated in vacuo and co-evaporated from toluene (×3) to give azetidin-3-yl diethylcarbamate trifluoracetate (Intermediate 20) (500 mg, 80%) as a gum.

The data for Intermediate 20 are in Table 2.

Route 4

Typical Procedure for the Preparation of Carbamates, as Exemplified by the Preparation of Intermediate 23, azetidin-3-yl 1,4-oxazepane-4-carboxylate hydrochloride To a stirred solution of tert-butyl 3-hydroxyazetidine-1-carboxylate (Intermediate 18) (400 mg, 2.31 mmol) in DCM (20 mL) was added TEA (1.6 mL, 11.6 mmol). The reaction was stirred at room temperature for 15 min and then cooled to 0° C. To this was then added portion wise 4-nitrophenyl carbonochloridate (Intermediate 19) (1.6 g, 8.09 mmol) and the reaction was then warmed to room temperature and stirred for 4 h.

To this was then added 1,4-oxazepane (Intermediate 10) (310 mg, 2.31 mmol) and the reaction was stirred at room temperature for 16 h. The reaction mixture was partitioned between H$_2$O (5 mL) and DCM (20 mL). The organics were dried (Na$_2$SO$_4$), concentrated in vacuo and the residue was purified by column chromatography (neutral alumina, EtOAc in hexane) to give 1-(tert-butoxycarbonyl)azetidin-3-yl 1,4-oxazepane-4-carboxylate (200 mg, 28%) as a gum.

LCMS (System 3, Method E): m/z 301 (M+H)$^+$ (ESI+ve), at 3.37 min, 202 nm.

To the stirred solution of 1-(tert-butoxycarbonyl)azetidin-3-yl 1,4-oxazepane-4-carboxylate (400 mg 1.33 mmol) in 1,4-dioxane (5 ml) at 0° C. was added HCl solution in 1,4-dioxane (4 M, 5 mL, 20 mmol) drop-wise. The reaction was warmed to room temperature and stirred for 3 h. The reaction mixture was concentrated in vacuo and triturated with diethyl ether and pentane to give azetidin-3-yl 1,4-oxazepane-4-carboxylate hydrochloride (Intermediate 23) (200 mg, 75%) as a gum.

The data for Intermediate 23 are in Table 2.

Route 5

Typical Procedure for the Preparation of Alcohols, as Exemplified by the Preparation of Intermediate 34, ethyl 5-(3-hydroxyazetidin-1-yl)-2-azabicyclo[2.2.2]octane-2-carboxylate

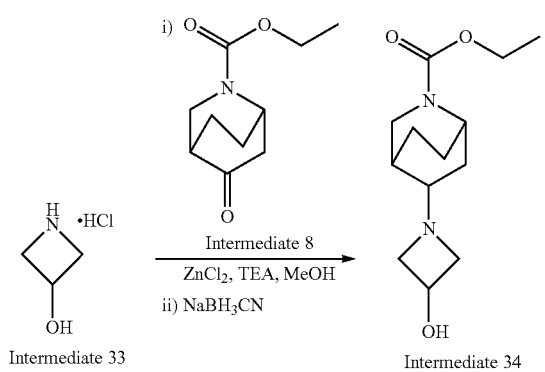

To a solution of azetidin-3-ol hydrochloride (Intermediate 33) (500 mg, 4.59 mmol) and TEA (3.18 mL, 22.9 mmol) in MeOH (10 mL) were added ethyl 5-oxo-2-azabicyclo[2.2.2]octane-2-carboxylate (Intermediate 8) followed by ZnCl₂ solution in diethyl ether (1 M, 0.23 mL, 0.23 mmol). The reaction mixture was stirred at 80° C. for 5 h and then cooled to 0° C. NaBH₃CN (853 mg, 13.7 mmol) was added and the reaction was warmed to room temperature and stirred for 18 h. The reaction mixture was partitioned between H₂O (150 mL) and EtOAc (40 mL). The aqueous layer was further extracted with EtOAc (2×40 mL) and the combined organic phases were dried (Na₂SO₄), concentrated in vacuo and the residue was purified by column chromatography (neutral alumina, 0 to 4% MeOH in DCM) to give ethyl 5-(3-hydroxyazetidin-1-yl)-2-azabicyclo[2.2.2]octane-2-carboxylate (Intermediate 34) (400 mg, 34%) as a liquid.

The data for Intermediate 34 are in Table 2.

General Synthetic Procedures:

Route A

Typical procedure for the preparation of amides as exemplified by the preparation of Example 1-1, ethyl-3-(3-(2-(diethylamino)-2-oxoethyl)azetidin-1-yl)-8-azabicyclo[3.2.1]octane-8-carboxylate

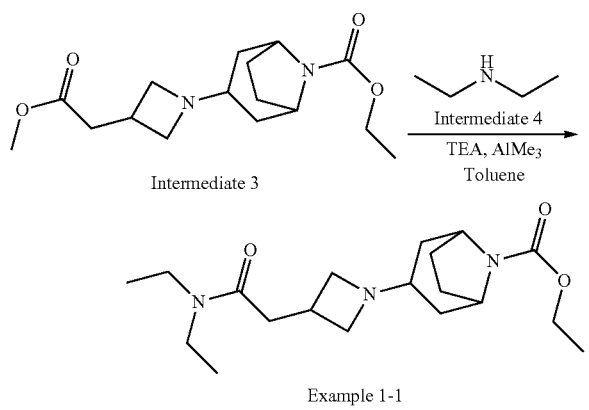

To a solution of diethylamine (Intermediate 4) (99 mg, 1.35 mmol) in toluene (10 mL) was added TEA (0.2 mL, 1.35 mmol). The reaction was then cooled to −10° C. and to this was then added trimethylaluminum solution in toluene (2.0 M, 0.7 mL, 1.35 mmol) and the reaction mixture was stirred at −10° C. to 0° C. for 20 mins followed by the addition of ethyl-3-(3-(2-methoxy-2-oxoethyl)azetidin-1-yl)-8-azabicyclo[3.2.1]octane-8-carboxylate (Intermediate 3) (140 mg, 0.45 mmol) at −10° C. The resulting reaction mixture was then stirred at 80° C. for 50 h. The solvents were removed in vacuo and the residue was partitioned between H₂O (10 mL) and DCM (80 mL), further extracting the aqueous layer with DCM (2×80 mL). The combined organic phases were dried (Na₂SO₄), concentrated in vacuo and the residue was purified by purification method A to give ethyl-3-(3-(2-(diethylamino)-2-oxoethyl)azetidin-1-yl)-8-azabicyclo[3.2.1]octane-8-carboxylate, Example 1-1 Isomer 1 (4 mg, 3%) as a yellow gum and ethyl-3-(3-(2-(diethylamino)-2-oxoethyl)azetidin-1-yl)-8-azabicyclo[3.2.1]octane-8-carboxylate, Example 1-1 Isomer 2 (47 mg, 30%) as a gum.

The data for Example 1-1 Isomer 2 are in Table 3.

Route B

Typical Procedure for the Preparation of Amines as Exemplified by the Preparation of Example 4-1, ethyl 6-(3-((diethylcarbamoyl)oxy)azetidin-1-yl)-2-azaspiro[3.3]heptane-2-carboxylate

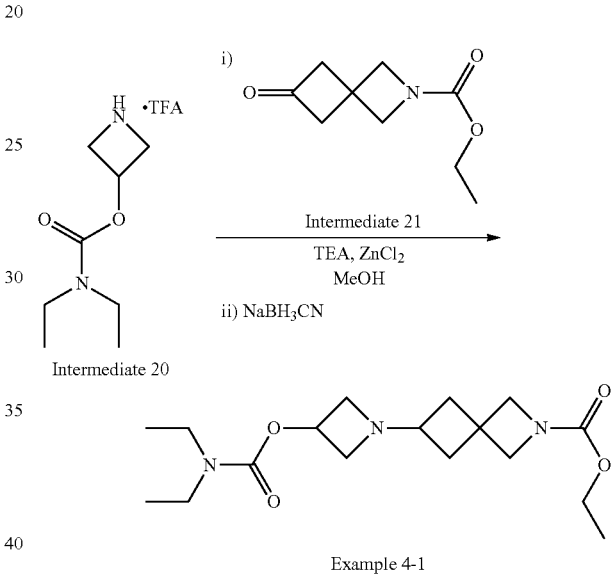

A solution of azetidin-3-yl diethylcarbamate trifluoroacetate (Intermediate 20) (200 mg, 1.16 mmol) and TEA (0.5 mL, 3.49 mmol) in MeOH (2 mL) was stirred at room temperature for 15 min. To this was then added ethyl 6-oxo-2-azaspiro[3.3]heptane-2-carboxylate (Intermediate 21) (160 mg, 0.87 mmol), followed by a solution of ZnCl₂ in diethyl ether (1 M, 0.6 mL, 0.060 mmol). The reaction was stirred at 90° C. for 4 h and then cooled to 0° C. before the portion wise addition of NaBH₃CN (146 mg, 2.32 mmol). The resulting reaction mixture was stirred at 90° C. for 16 h. The solvents were removed in vacuo and the residue was partitioned between H₂O (200 mL) and EtOAc (200 mL), extracting the aqueous layer further with EtOAc (2×200 mL). The combined organic phases were dried (Na₂SO₄), concentrated in vacuo and the residue was purified by purification method M to give ethyl 6-(3-((diethylcarbamoyl)oxy)azetidin-1-yl)-2-azaspiro[3.3]heptane-2-carboxylate, Example 4-1 (35 mg, 9%) as a colourless gum.

The data for Example 4-1 are in Table 3.

Route C

Typical Procedure for the Preparation of Carbamates as Exemplified by the Preparation of Example 6-1, ethyl 5-(3-((diethylcarbamoyl)oxy)azetidin-1-yl)-2-azabicyclo[2.2.2]octane-2-carboxylate

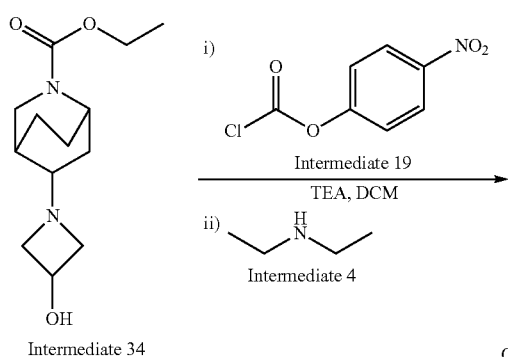

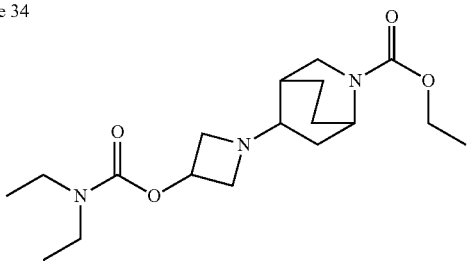

Example 6-1

To a solution of ethyl 5-(3-hydroxyazetidin-1-yl)-2-azabicyclo[2.2.2]octane-2-carboxylate (Intermediate 34) (100 mg, 0.39 mmol) in DCM (5 mL) at 0° C. were added TEA (0.1 mL, 1.18 mmol) followed by 4-nitrophenyl carbonochloridate (Intermediate 19) (94 mg, 0.47 mmol). The reaction mixture was stirred at 0° C. for 5 h. To this was then added diethylamine (Intermediate 4) (0.1 mL, 0.79 mmol) and the reaction was stirred at room temperature for 16 h. The reaction was partitioned between $H_2O$ (150 mL) and EtOAc (40 mL). The aqueous layer was further extracted with EtOAc (2×40 mL) and the combined organic phases were dried ($Na_2SO_4$), concentrated in vacuo and the residue was purified by purification method B1 to give ethyl-5-(3-((diethylcarbamoyl)oxy)azetidin-1-yl)-2-azabicyclo[2.2.2]octane-2-carboxylate, Example 6-1 Isomer 1 (28 mg, 20%) as a colourless gum and ethyl-5-(3-((diethylcarbamoyl)oxy)azetidin-1-yl)-2-azabicyclo[2.2.2]octane-2-carboxylate, Example 6-1 Isomer 2 (13 mg, 9%) as a colourless gum.

The data for Example 6-1 Isomer 1 are in Table 3.

TABLE 2

Starting Materials and Intermediates

| Intermediate Number | Name | Synthetic Route | Intermediates Used | Data |
|---|---|---|---|---|
| 1 | tert-Butyl 3-(2-methoxy-2-oxoethyl)azetidine-1-carboxylate | — | — | Commercially available, CAS: 497160-14-2 |
| 2 | Ethyl 3-oxo-8-azabicyclo[3.2.1]octane-8-carboxylate | — | — | Commercially available, CAS: 32499-64-2 |
| 3 | Ethyl-3-(3-(2-methoxy-2-oxoethyl)azetidin-1-yl)-8-azabicyclo[3.2.1]octane-8-carboxylate | 1 | 1 and 2 | LCMS (System 1, Method C): m/z 311 (M + H)+ (ESI + ve), at 4.85 min, 202 nm |
| 4 | Diethylamine | — | — | Commercially available, CAS: 109-89-7 |
| 5 | N-Ethylpropan-2-amine | — | — | Commercially available, CAS: 19961-27-4 |
| 6 | 1-Azaspiro[3.3]heptane oxalate | — | — | Commercially available, CAS: 1706457-37-5 |
| 7 | Piperidine | — | — | Commercially available, CAS: 110-89-4 |
| 8 | Ethyl 5-oxo-2-azabicyclo[2.2.2]octane-2-carboxylate | 2 | 12 and 13 | LCMS (System 1, Method C): m/z 198 (M + H)+ (ESI + ve), at 3.06 min, 202 nm Commercially available, CAS: 37778-51-1 |
| 9 | Ethyl-5-(3-(2-methoxy-2-oxoethyl)azetidin-1-yl)-2-azabicyclo[2.2.2]octane-2-carboxylate | 1 | 1 and 8 | LCMS (System 1, Method C): m/z 311 (M + H)+ (ESI + ve), at 3.68 min and 3.93 min, 202 nm |
| 10 | 1,4-Oxazepane | — | — | Commercially available, CAS: 5638-60-8 |
| 11 | 1-Azaspiro[3.3]heptane hydrochloride | — | — | Commercially available, CAS: 1986337-29-4 |
| 12 | tert-Butyl 5-oxo-2-azabicyclo[2.2.2]octane-2-carboxylate | — | — | Commercially available, CAS: 617714-22-4 |
| 13 | Ethyl carbonochloridate | — | — | Commercially available, CAS: 541-41-3 |
| 14 | Ethyl 3-oxo-9-azabicyclo[3.3.1]nonane-9-carboxylate | 2 | 13 and 17 | LCMS (System 1, Method C): m/z 212 (M + H)+ (ESI + ve), at 3.51 min, 202 nm Commercially available, CAS: 72761-58-1 |

TABLE 2-continued

Starting Materials and Intermediates

| Intermediate Number | Name | Synthetic Route | Intermediates Used | Data |
|---|---|---|---|---|
| 15 | Ethyl-3-(3-(2-methoxy-2-oxoethyl)azetidin-1-yl)-9-azabicyclo[3.3.1]nonane-9-carboxylate | 1 | 1 and 14 | LCMS (System 1, Method C): m/z 325 (M + H)$^+$ (ESI + ve), at 3.97 min, 202 nm |
| 16 | Pyrrolidine | — | — | Commercially available, CAS: 123-75-1 |
| 17 | tert-Butyl 3-oxo-9-azabicyclo[3.3.1]nonane-9-carboxylate | — | — | Commercially available, CAS: 512822-27-4 |
| 18 | tert-Butyl 3-hydroxyazetidine-1-carboxylate | — | — | Commercially available, CAS: 141699-55-0 |
| 19 | 4-Nitrophenyl carbonochloridate | — | — | Commercially available, CAS: 7693-46-1 |
| 20 | Azetidin-3-yl diethylcarbamate trifluoroacetate | 3 | 4, 18 and 19 | LCMS (System 1, Method E): m/z 173 (M + H)$^+$ (ESI + ve), at 2.14 min, 202 nm |
| 21 | Ethyl 6-oxo-2-azaspiro[3.3]heptane-2-carboxylate | — | — | As prepared in WO 2017021728 CAS: 2011798-96-0 |
| 22 | Ethyl 2-oxo-6-azaspiro[3.4]octane-6-carboxylate | — | — | As prepared in WO 2017021729 CAS: 1803350-92-6 |
| 23 | Azetidin-3-yl 1,4-oxazepane-4-carboxylate hydrochloride | 4 | 10, 18 and 19 | LCMS (System 3, Method E): m/z 201 (M + H)$^+$ (ESI + ve), at 0.71 min, 202 nm |
| 24 | Ethyl 6-oxo-2-azaspiro[3.4]octane-2-carboxylate | — | — | As prepared in WO 2017021728 CAS: 2011798-97-1 |
| 25 | Azetidin-3-yl ethyl(methyl)carbamate trifluoroacetate | 3 | 18, 19 and 26 | LCMS (System 4, Method B): m/z 159 (M + H)$^+$ (ESI + ve), at 2.95 min, 202 nm |
| 26 | N-Methylethanamine | — | — | Commercially available, CAS: 624-78-2 |
| 27 | Methyl 6-oxo-2-azaspiro[3.4]octane-2-carboxylate | — | — | As prepared in WO 2017021728 CAS: 2077964-94-2 |
| 28 | Azetidin-3-yl pyrrolidine-1-carboxylate hydrochloride | 4 | 16, 18 and 19 | LCMS (System 2, Method D): m/z 171 (M + H)$^+$ (ESI + ve), at 0.50 min, 202 nm |
| 29 | Morpholine | — | — | Commercially available, CAS: 110-91-8 |
| 30 | Azetidin-3-yl morpholine-4-carboxylate trifluoroacetate | 3 | 18, 19 and 29 | LCMS (System 4, Method B): m/z 187 (M + H)$^+$ (ESI + ve), at 2.37 min, 202 nm |
| 31 | Azepane | — | — | Commercially available, CAS: 111-49-9 |
| 32 | Azetidin-3-yl azepane-1-carboxylate trifluoroacetate | 3 | 18, 19 and 31 | LCMS (System 3, Method E): m/z 199 (M + H)$^+$ (ESI + ve), at 2.48 min, 202 nm |
| 33 | Azetidin-3-ol hydrochloride | — | — | Commercially available, CAS: 18621-18-6 |
| 34 | Ethyl 5-(3-hydroxyazetidin-1-yl)-2-azabicyclo[2.2.2]octane-2-carboxylate | 5 | 8 and 33 | LCMS (System 1, Method E): m/z 255 (M + H)$^+$ (ESI + ve), at 2.47, 2.64 min, 202 nm |
| 35 | tert-Butyl 7-oxo-3-oxa-9-azabicyclo[3.3.1]nonane-9-carboxylate | — | — | Commercially available, CAS: 280761-97-9 |
| 36 | Ethyl 7-oxo-3-oxa-9-azabicyclo[3.3.1]nonane-9-carboxylate | 2 | 13 and 35 | LCMS (System 2, Method A): m/z 214 (M + H)$^+$ (ESI + ve), at 1.53 min, 202 nm |

TABLE 3

NMR and LCMS properties and the methods used to prepare and purify compunds represented by Examples 1-1 to 8-1

| Ex. No. | Name | Synthetic Method and Intermediates Used | Purification Method | ¹H NMR | LCMS System and Method | LCMS data |
|---|---|---|---|---|---|---|
| 1-1 | Isomer 2: Ethyl-3-(3-(2-(diethylamino)-2-oxoethyl)azetidin-1-yl)-8-azabicyclo[3.2.1]octane-8-carboxylate | A 3 and 4 | A | ¹H NMR (400 MHz, Methanol-$d_4$) δ 1.06-1.14 (m, 3H), 1.17-1.29 (m, 6H), 1.51-1.55 (m, 1H), 1.56-1.60 (m, 1H), 1.68-1.82 (m, 2H), 1.82-1.96 (m, 2H), 2.06-2.20 (m, 2H), 2.37-2.47 (m, 1H), 2.55-2.69 (m, 4H), 2.69-2.79 (m, 2H), 3.33-3.44 (m, 5H), 3.99-4.26 (m, 4H) | 1 C | m/z 352 (M + H)⁺ (ES⁺), at 4.49 min, 210 nm |
| 1-2 | Isomer mixture: Ethyl-3-(3-(2-(ethyl(isopropyl)amino)-2-oxoethyl)azetidin-1-yl)-8-azabicyclo[3.2.1]octane-8-carboxylate | A 3 and 5 | B | ¹H NMR (400 MHz, Methanol-$d_4$) δ 1.07-1.28 (m, 12H), 1.50-1.60 (m, 2H), 1.64-1.81 (m, 2H), 1.82-1.95 (m, 2H), 2.01-2.19 (m, 2H), 2.35-2.47 (m, 1H), 2.55-2.79 (m, 5H), 4.05-4.67 (m, 4H) Five protons obscured by solvent peaks | 3 E | m/z 366 (M + H)⁺ (ES⁺), at 4.09 min, 202 nm |
| 1-3 | Isomer 2: Ethyl-3-(3-(2-oxo-2-(1-azaspiro[3.3]heptan-1-yl)ethyl)azetidin-1-yl)-8-azabicyclo[3.2.1]octane-8-carboxylate | A 3 and 6 | C | ¹H NMR (400 MHz, Methanol-$d_4$) δ 1.17-1.31 (m, 3H), 1.49-1.61 (m, 2H), 1.64-1.93 (m, 6H), 1.96-2.21 (m, 4H), 2.22-2.49 (m, 5H), 2.52-2.78 (m, 3H), 2.79-3.01 (m, 2H), 3.19-3.31 (m, 2H), 3.73-4.06 (m, 2H), 4.06-4.20 (m, 4H) | 3 E | m/z 376 (M + H)⁺ (ES⁺), at 4.10 min, 202 nm |
| 1-4 | Isomer mixture: Ethyl-3-(3-(2-oxo-2-(piperidin-1-yl)ethyl)azetidin-1-yl)-8-azabicyclo[3.2.1]octane-8-carboxylate | A 3 and 7 | D | ¹H NMR (400 MHz, Methonal-$d_4$) δ 1.20-1.28 (m, 3H), 1.45-1.81 (m, 9H), 1.82-1.96 (m, 2H), 2.06-2.20 (m, 2H), 2.31-2.48 (m, 1H), 2.55-2.91 (m, 5H), 3.34-3.38 (m, 1H), 3.45-3.62 (m, 3H), 4.01-4.50 (m, 4H) Three protons obscured by solvent peaks | 1 C | m/z 364 (M + H)⁺ (ES⁺), at 5.02 min, 210 nm |
| 2-1 | Isomer 1: Ethyl-5-(3-(2-(diethylamino)-2-oxoethyl)azetidin-1-yl)-2-azabicyclo[2.2.2]octane-2-carboxylate | A 4 and 9 | E | ¹H NMR (400 MHz, Methanol-$d_4$) δ 1.02-1.32 (m, 11H), 1.37-1.53 (m, 1H), 1.59-2.06 (m, 5H), 2.49-2.73 (m, 3H), 2.77-2.92 (m, 2H), 3.22-3.29 (m, 1H), 3.33-3.50 (m, 5H), 3.52-3.72 (m, 2H), 3.88-4.01 (m, 1H), 4.04-4.18 (m, 2H) | 1 C | m/z 352 (M + H)⁺ (ES⁺), at 3.62 min, 202 nm |
| 2-2 | Isomer 1: Ethyl-5-(3-(2-(ethyl(isopropyl)amino)-2-oxoethyl)azetidin-1-yl)-2-azabicyclo[2.2.2]octane-2-carboxylate | A 5 and 9 | F | ¹H NMR (400 MHz, Methanol-$d_4$) δ 1.02-1.33 (m, 14H), 1.36-2.06 (m, 5H), 2.50-2.61 (m, 1H), 2.62-2.73 (m, 2H), 2.75-2.95 (m, 3H), 3.19-3.30 (m, 2H), 3.33-3.51 (m, 3H), 3.52-3.66 (m, 1H), 3.90-4.02 (m, 1H), 4.05-4.61 (m, 2H) One proton obscured by solvent peaks | 1 C | m/z 366 (M + H)⁺ (ES⁺), at 4.01 min, 210 nm |
| 2-2 | Isomer 2: Ethyl-5-(3-(2-(ethyl(isopropyl)amino)-2-oxoethyl)azetidin-1-yl)-2-azabicyclo[2.2.2]octane-2-carboxylate | A 5 and 9 | F | ¹H NMR (400 MHz, Methanol-$d_4$) δ 1.02-1.32 (m, 13H), 1.34-1.49 (m, 1H), 1.51-2.02 (m, 6H), 2.46-2.60 (m, 1H), 2.62-2.94 (m, 5H), 3.12-3.27 (m, 2H), 3.38-3.66 (m, 3H), 3.90-4.02 (m, 1H) 4.04-4.62 (m, 3H) | 1 C | m/z 366 (M + H)⁺ (ES⁺), at 4.27 min, 210 nm |
| 2-3 | Isomer 1: Ethyl-5-(3-(2-oxo-2-(piperidin-1-yl)ethyl)azetidin-1-yl)-2-azabicyclo[2.2.2]octane-2-carboxylate | A 7 and 9 | G | ¹H NMR (400 MHz, Methanol-$d_4$) δ 1.20-1.30 (m, 6H), 1.39-1.94 (m, 12H), 2.10-2.52 (m, 2H), 2.56-3.26 (m, 3H), 3.34-3.76 (m, 7H), 3.91-4.29 (m, 3H) | 1 E | m/z 364 (M + H)⁺ (ES⁺), at 4.06 min, 202 nm |
| 2-4 | Isomer 1: Ethyl-5-(3-(2-(1,4-oxazepan-4-yl)-2-oxoethyl)azetidin-1-yl)-2-azabicyclo[2.2.2]octane-2-carboxylate | A 9 and 10 | H | ¹H NMR (400 MHz, Methanol-$d_4$) δ 1.15-1.30 (m, 4H), 1.35-1.55 (m, 1H) 1.60-2.04 (m, 7H), 2.47-2.60 (m, 1H), 2.62-2.94 (m, 5H), 3.23-3.29 (m, 1H), 3.33-3.52 (m, 2H), 3.53-3.84 (m, 9H), 3.91-4.00 (m, 1H), 4.02-4.18 (m, 2H) | 3 E | m/z 380 (M + H)⁺ (ES⁺), at 2.48 min, 202 nm |
| 2-5 | Isomer 1: Ethyl-5-(3-(2-oxo-2-(1-azaspiro[3.3]heptan-1-yl)ethyl)azetidin-1-yl)-2-azabicyclo[2.2.2]octane-2-carboxylate | A 9 and 11 | I | ¹H NMR (400 MHz, Methanol-$d_4$) δ 2.08-2.29 (m, 4H), 2.33-2.47 (m, 1H), 2.55-3.07 (m, 8H), 3.14-3.26 (m, 1H), 3.34-3.43 (m, 1H), 3.43-3.56 (m, 4H), 3.57-4.01 (m, 5H), 4.15-4.58 (m, 4H), 4.66-5.00 (m, 3H), 5.01-5.18 (m, 2H) Three protons obscured by solvent peaks | 1 C | m/z 376 (M + H)⁺ (ES⁺), at 3.97 min, 210 nm |
| 3-1 | Isomer 1: Ethyl-3-(3-(2-(diethylamino)-2-oxoethyl)azatidin-1-yl)-9-azabicyclo[3.3.1]nonane-9-carboxylate | A 4 and 15 | J | ¹H NMR (400 MHz, Methanol-$d_4$) δ 1.01-1.12 (m, 5H), 1.15-1.30 (m, 6H), 1.38-1.67 (m, 5H). 1.90-2.24 (m, 4H), 2.54-2.71 (m, 2H), 2.73-2.94 (m, 3H), 3.33-3.43 (m, 4H), 3.47-3.56 (m, 2H), 4.02-4.21 (m, 2H), 4.33-4.53 (m, 2H) | 1 E | m/z 366 (M + H)⁺ (ES⁺), at 3.38 min, 202 nm |

TABLE 3-continued

NMR and LCMS properties and the methods used to prepare and purify compunds represented by Examples 1-1 to 8-1

| Ex. No. | Name | Synthetic Method and Intermediates Used | Purification Method | ¹H NMR | LCMS System and Method | LCMS data |
|---|---|---|---|---|---|---|
| 3-2 | Isomer 1: Ethyl-3-(3-(2-oxo-2-(pyrrolidin-1-yl)-9-azabicyclo[3.3.1]nonane-9-carboxylate | A 15 and 16 | K | ¹H NMR (400 MHz, Methanol-d4) δ 1.01-1.16 (m, 2H), 1.23-1.30 (m, 3H), 1.39-1.67 (m, 6H), 1.83-1.92 (m, 2H), 1.93-2.25 (m, 4H), 2.57-2.66 (m, 2H), 3.35-3.41 (m, 3H), 3.44-3.56 (m, 4H), 4.05-4.19 (m, 2H), 4.38-4.51 (m, 2H) | 1 E | m/z 364 (M + H)+ (ES+), at 4.10 min, 214 nm |
| 3-3 | Isomer 1: Ethyl-3-(3-(2-oxo-2-(piperidin-1-yl)ethyl)azetidin-1-yl)-9-azabicyclo[3.3.1]nonane-9-carboxylate | A 7 and 15 | L | ¹H NMR (400 MHz, Methanol-d4) δ 1.02-1.13 (m, 2H), 1.22-1.30 (m, 3H), 1.37-1.74 (m, 11H), 1.89-2.23 (m, 4H), 2.61-2.69 (m, 2H), 2.73-2.94 (m, 3H), 3.42-3.59 (m, 6H), 4.04-3.59 (m, 6H), 4.04-4.19 (m, 2H), 4.36-4.54 (m, 2H) | 1 E | m/z 378 (M + H)+ (ES+), at 3.45 min, 202 nm |
| 4-1 | Ethyl 6-(3-((diethylcarbamoyl)oxy)azetidin-1-yl)-2-azaspiro[3.3]heptane-2-carboxylate | B 20 and 21 | M | ¹H NMR (400 MHz, Methanol-d4) δ 1.07-1.19 (m, 6H), 1.22 (t, J = 7.1 Hz, 3H), 1.96-2.07 (m, 2H), 2.23-2.33 (m, 2H), 3.05-3.16 (m, 4H), 3.55-3.64 (m, 2H), 3.84-3.92 (m, 2H), 3.93-4.00 (m, 2H), 3.93-4.00 (m, 2H), 4.06 (q, J = 7.1 Hz, 2H), 4.91-5.00 (m, 1H) Three protons obscured by solvent peaks | 1 E | m/z 340 (m + H)+ (ES+), at 3.83 min, 202 nm |
| 4-2 | Isomer 2: Ethyl 2-(3-((diethylcarbamoyl)oxy)azatidin-1-yl)-6-azaspiro[3.4]octane-6-carboxylate | B 20 and 22 | N | ¹H NMR (400 MHz, Methanol-d4) δ 1.04-1.20 (m, 6H), 1.25 (t, J = 7.1 Hz, 3H), 1.83-1.98 (m, 4H), 2.00-2.13 (m, 2H), 3.17-3.29 (m, 5H), 3.34-3.44 (m, 3H), 3.62-3.77 (m, 2H), 4.09 (q, J = 7.1 Hz, 2H) 4.94-5.02 (m, 1H) Three protons obscured by solvent peaks | 1 E | m/z 354 (M + H)+ (ES+), at 4.05 min, 202 nm |
| 4-3 | Isomer 2: 1-(6-(Ethoxycarbonyl)-6-azaspiro[3.4]octan-2-yl)azetidin-3-yl 1,4-oxazepane-4-carboxylate | B 22 and 23 | O | ¹H NMR (400 MHz, Methanol-d4) δ 1.20-1.28 (m, 3H), 1.80-1.97 (m, 6H), 1.99-2.09 (m, 2H), 3.12-3.20 (m, 2H), 3.21-3.29 (m, 3H), 3.33-3.41 (m, 2H), 3.51-3.65 (m, 6H), 3.68-3.78 (m, 4H), 4.05-4.14 (m, 2H), 4.94-5.02 (m, 1H) | 3 E | m/z 382 (M + H)+ (ES+), at 3.04 min, 202 nm |
| 4-4 | Isomer 1: Ethyl 6-(3-((ethyl(methyl)carbamoyl)oxy)azetidin-1-yl)-2-azaspiro[3.4]octane-2-carboxylate | B 24 and 25 | P then Q | ¹H NMR (400 MHz, Methanol-d4) δ 1.04-1.18 (m, 3H), 1.22 (t, J = 7.1 Hz, 3H), 1.35-1.46 (m, 1H), 1.53-1.64 (m, 1H), 1.69-2.08 (m, 4H), 2.82-2.97 (m, 4H), 3.02-3.15 (m, 2H), 3.59-3.67 (m, 2H), 3.71-3.93 (m, 4H), 4.07 (q, J = 7.1 Hz, 2H) Three protons obscured by solvent peaks | 4 B | m/z 340 (M + H)+ (ES+), at 5.01 min, 202 nm |
| 4-5 | Isomer 1: Ethyl 6-(3-((diethylcarbamoyl)oxy)azetidin-1-yl)-2-azaspiro[3.4]octane-2-carboxylate | B 20 and 24 | R then S | ¹H NMR (400 MHz, Methanol-d4) δ 1.05-1.18 (m, 6H), 1.22 (t, J = 7.1 Hz, 3H), 1.34-1.47 (m, 1H), 1.53-1.63 (m, 1H), 1.69-1.88 (m, 2H), 1.88-2.05 (m, 2H), 2.80-2.95 (m, 1H), 3.03-3.14 (m, 2H), 3.58-3.69 (m, 2H), 3.72-3.93 (m, 4H), 4.07 (q, J = 7.1 Hz, 2H), 4.91-5.02 (m, 2H) Three protons obscured by solvent peaks | 3 E | m/z 354 (m + H)+ (ES+), at 3.72 min, 202 nm |
| 4-5 | Isomer 2: Ethyl 6-(3-((diethylcarbamoyl)oxy)azetidin-1-yl)-2-azaspiro[3.4]octane-2-carboxylate | B 20 and 24 | R then S | ¹H NMR (400 MHz, Methanol-d4) δ 1.04-1.18 (m, 6H), 1.22 (t, J = 7.1 Hz, 3H), 1.34-1.48 (m, 1H), 1.53-1.64 (m, 1H), 1.70-1.88 (m, 2H), 1.89-2.05 (m, 2H), 2.82-2.92 (m, 1H), 3.02-3.13 (m, 2H), 3.58-3.70 (m, 2H), 3.71-3.94 (m, 4H), 4.06 (q, J = 7.1 Hz, 2H), 4.90-5.01 (m, 2H) Three protons obscured by solvent peaks | 3 E | m/z 354 (M + H)+ (ES+), at 3.74 min, 202 nm |
| 4-6 | Isomer 1: Methyl 6-(3-((diethylcarbamoyl)oxy)azetidin-1-yl)-2-azaspiro[3.4]octane-2-carboxylate | B 20 and 27 | T | ¹H NMR (400 MHz, Methanol-d4) δ 1.04-1.23 (m, 6H), 1.35-1.49 (m, 1H), 1.54-1.66 (m, 1H), 1.72-1.89 (m, 2H), 1.90-2.07 (m, 2H), 2.82-2.89 (m, 1H), 3.07-3.18 (m, 2H), 3.59-3.72 (m, 5H), 3.73-3.99 (m, 4H) Five protons obscured by solvent peaks | 4 B | m/z 340 (M + H)+ (ES+), at 4.78 min, 202 nm |
| 4-6 | Isomer 2: Methyl 6-(3-((diethylcarbamoyl)oxy)azetidin-1-yl)-2-azaspiro[3.4]octane-2-carboxylate | B 20 and 27 | T | ¹H NMR (400 MHz, Methanol-d4) δ 1.03-1.23 (m, 6H), 1.33-1.49 (m, 1H), 1.53-1.64 (m, 1H), 1.70-1.88 (m, 2H), 1.89-2.08 (m, 2H), 2.79-2.97 (m, 1H), 3.02-3.16 (m, 2H), 3.57-3.70 (m, 5H), 3.72-4.00 (m, 4H) Five protons obscured by solvent peaks | 4 B | m/z 340 (m + H)+ (ES+), at 4.95 min, 202 nm |

TABLE 3-continued

NMR and LCMS properties and the methods used to prepare and purify compunds represented by Examples 1-1 to 8-1

| Ex. No. | Name | Synthetic Method and Intermediates Used | Purification Method | $^1$H NMR | LCMS System and Method | LCMS data |
|---|---|---|---|---|---|---|
| 4-7 | Isomer 1: Ethyl 6-(3-((pyrrolidine-1-carbonyl)oxy)azetidin-1-yl)-2-azaspiro[3.4]octane-2-carboxylate | B 24 and 28 | U then V | $^1$H NMR (400 MHz, Methanol-δ4) δ 1.22 (t, J = 7.1 Hz, 3H), 1.34-1.48 (m, 1H), 1.53-1.64 (m, 1H), 1.70-2.07 (m, 8H), 2.82-2.93 (m, 1H), 3.04-3.15 (m, 2H), 3.35-3.44 (m, 2H), 3.58-3.69 (m, 2H), 3.73-3.92 (m, 4H), 4.07 (q, J = 7.1 Hz, 2H), 4.90-4.98 (m, 1H) Two protons obscured by solvent peaks | 3 E | m/z 352 (M + H)$^+$ (ES$^+$), at 3.27 min, 202 nm |
| 4-8 | Isomer 1: 1-(2-(Ethoxycarbonyl)-2-azaspiro[3.4]octane-6-yl)azetidin-3-yl morpholine-4-carboxylate | B 24 and 30 | W then X | $^1$H NMR (400 MHz, Methanol-δ4) δ 1.22 (t, J = 7.1 Hz, 3H), 1.35-1.46 (m, 1H), 1.53-1.63 (m, 1H), 1.69-1.87 (m, 2H), 1.89-2.06 (m, 2H), 2.81-2.94 (m, 1H), 3.03-3.17 (m, 2H), 3.37-3.55 (m, 4H), 3.58-3.69 (m, 6H), 3.72-3.95 (m, 4H), 4.07 (q, J = 7.1 Hz, 2H), 4.91-4.98 (m, 1H) | 3 E | m/z 368 (M + H)$^+$ (ES$^+$), at 3.06 min, 202 nm |
| 4-9 | Isomer 1: 1-(2-(Ethoxycarbonyl)-2-azaspiro[3.4]octane-6-yl)azetidin-3-yl 1,4-oxazepane-4-carboxylate | B 23 and 24 | Y then V | $^1$H NMR (400 MHz, Methanol-δ4) δ 1.23 (t, J = 7.1 Hz, 3H), 1.38-1.52 (m, 1H), 1.57-1.69 (m, 1H), 1.77-2.02 (m, 5H), 2.05-2.18 (m, 1H), 3.05-3.20 (m, 1H), 3.34-3.45 (m, 2H), 3.51-3.66 (m, 4H), 3.69-3.96 (m, 10H), 4.07 (q, J = 7.1 Hz, 2H), 4.96-5.06 (m, 1H) | 3 E | m/z 382 (M + H)$^+$ (ES$^+$), at 2.97 min, 202 nm |
| 4-9 | Isomer 2: 1-(2-(Ethoxycarbonyl)-2-azaspiro[3.4]octane-6-yl)azetidin-3-yl 1,4-oxazepane-4-carboxylate | B 23 and 24 | Y then V | $^1$H NMR (400 MHz, Methanol-δ4) δ 1.23 (t, J = 7.1 Hz, 3H), 1.35-1.47 (m, 1H), 1.53-1.65 (m, 1H), 1.70-2.07 (m, 6H), 2.82-2.95 (m, 1H), 3.04-3.17 (m, 2H), 3.51-3.68 (m, 6H), 3.69-3.95 (m, 8H), 4.07 (q, J = 7.1 Hz, 2H), 4.92-5.01 (m, 1H) | 3 E | m/z 382 (M + H)$^+$ (ES$^+$), at 2.97 min, 202 nm |
| 5-1 | Isomer mixture: Ethyl 3-(3-((azepane-1-carbonyl)oxy)azetidin-1-yl)-8-azabicyclo[3.2.1]octane-8-carboxylate | B 2 and 32 | Z | $^1$H NMR (400 MHz, Methanol-δ4) δ 1.22-1.28 (m, 3H), 1.53-1.63 (m, 6H), 1.66-1.93 (m, 8H), 2.05-2.17 (m, 2H), 2.77-2.92 (m, 2H), 3.37-3.47 (m, 4H), 3.57-3.70 (m, 2H), 4.05-4.22 (m, 4H) Two protons obscured by solvent peaks | 3 E | m/z 380 (M + H)$^+$ (ES$^+$), at 5.17 min, 202 nm |
| 5-2 | Isomer mixture: 1-(8-(Ethoxycarbonyl)-8-azabicyclo[3.2.1]octane-3-yl)azetidin-3-yl 1,4-oxazepane-4-carboxylate | B 2 and 23 | AA | $^1$H NMR (400 MHz, Methanol-δ4) δ 1.18-1.29 (m, 3H), 1.52-1.64 (m, 2H), 1.67-1.96 (m, 6H), 2.00-2.18 (m, 2H), 2.40-2.55 (m, 1H), 2.77-2.93 (m, 2H), 3.51-3.61 (m, 4H), 3.61-3.68 (m, 2H), 3.68-3.80 (m, 3H), 4.02-4.25 (m, 4H) Two protons obscured by solvent peaks | 3 E | m/z 382 (M + H)$^+$ (ES$^+$), at 3.85 min, 202 nm |
| 6-1 | Isomer 1: Ethyl 5-(3-((diethylcarbamoyl)oxy)azetidin-1-yl)-2-azabicyclo[2.2.2]octane-2-carboxylate | C 4, 19, and 34 | AB | $^1$H NMR (400 MHz, Methanol-δ4) δ 1.02-1.20 (m, 6H), 1.20-1.33 (m, 4H), 1.38-1.52 (m, 1H), 1.61-1.88 (m, 3H), 1.89-2.07 (m, 2H), 2.53-2.65 (m, 1H), 2.98-3.10 (m, 2H), 3.38-3.47 (m, 1H), 3.59-3.68 (m, 1H), 3.71-3.79 (m, 1H), 3.92-4.01 (m, 1H), 4.05-4.18 (m, 2H), 4.94-5.02 (m, 1H) Five protons obscured by solvent peaks | 1 E | m/z 354 (M + H)$^+$ (ES$^+$), at 4.19 min, 202 nm |
| 6-2 | Isomer 1: Ethyl 5-(3-((pyrrolidine-1-carbonyl)oxy)azetidin-1-yl)-2-azabicyclo[2.2.2]octane-2-carboxylate | C 16, 19, and 34 | AC | $^1$H NMR (400 MHz, Methanol-δ4) δ 1.17-1.32 (m, 4H), 1.37-1.53 (m, 1H), 1.62-2.08 (m, 9H), 2.51-2.64 (m, 1H), 3.00-3.12 (m, 2H), 3.36-3.48 (m, 3H), 3.57-3.66 (m, 1H), 3.69-3.78 (m, 1H), 3.91-4.01 (m, 1H), 4.05-4.17 (m, 2H), 4.92-5.04 (m, 1H) Three protons obscured by solvent peaks | 1 E | m/z 352 (M + H)$^+$ (ES$^+$), at 3.93 min, 202 nm |
| 6-3 | Isomer 1: Ethyl 5-(3-((piperidine-1-carbonyl)oxy)azetidin-1-yl)-2-azabicyclo[2.2.2]octane-2-carboxylate | C 7, 19, and 34 | AD | $^1$H NMR (400 MHz, Methanol-δ4) δ 1.19-1.31 (m, 4H), 1.38-1.58 (m, 5H), 1.59-1.87 (m, 5H), 1.88-2.08 (m, 2H), 2.52-2.66 (m, 1H), 2.99-3.12 (m, 2H), 3.34-3.52 (m, 5H), 3.57-3.66 (m, 1H), 3.68-3.76 (m, 1H), 3.92-3.99 (m, 1H), 4.04-4.16 (m, 2H), 4.92-5.01 (m, 1H) One proton obscured by solvent peaks | 1 E | m/z 366 (M + H)$^+$ (ES$^+$), at 4.28 min, 202 nm |

TABLE 3-continued

NMR and LCMS properties and the methods used to prepare and purify compunds represented by Examples 1-1 to 8-1

| Ex. No. | Name | Synthetic Method and Intermediates Used | Purification Method | $^1$H NMR | LCMS System and Method | LCMS data |
|---|---|---|---|---|---|---|
| 6-4 | Isomer 1: Ethyl 5-(3-((azepane-1-carbonyl)oxy)azetidin-1-yl)-2-azabicyclo[2.2.2]octane-2-carboxylate | B 8 and 32 | AE | $^1$H NMR (400 MHz, Methanol-d4) δ 1.19-1.30 (m, 4H), 1.38-1.50 (m, 1H), 1.52-1.62 (m, 4H), 1.63-2.07 (m, 9H), 2.52-2.63 (m, 1H), 2.99-3.09 (m, 2H), 3.33-3.37 (m, 1H), 3.38-3.52 (m, 5H), 3.57-3.67 (m, 1H), 3.69-3.79 (m, 1H), 3.90-4.01 (m, 1H), 4.03-4.19 (m, 2H), 4.92-5.03 (m, 1H) | 3 E | m/z 380 (M + H)$^+$ (ES$^+$), at 3.99 min, 202 nm |
| 6-5 | Isomer 1: 1-(2-(Ethoxycarbonyl)-2-azabicyclo[2.2.2]octane-5-yl)azetidin-3-yl 1,4-oxazepane-4-carboxylate | B 8 and 23 | AF | $^1$H NMR (400 MHz, Methanol-d4) δ 1.18-1.32 (m, 5H), 1.39-1.52 (m, 1H), 1.59-2.07 (m, 6H), 2.53-2.67 (m, 1H), 3.03-3.13 (m, 2H), 3.34-3.51 (m, 2H), 3.51-3.68 (m, 5H), 3.68-3.79 (m, 5H), 3.91-4.00 (m, 1H), 4.03-4.17 (m, 2H), 4.94-5.04 (m, 1H) | 3 E | m/z 382 (M + H)$^+$ (ES$^+$), at 2.98 min, 202 nm |
| 7-1 | Isomer 1: Ethyl 3-(3-((diethylcarbamoyl)oxy)azetidin-1-yl)-9-azabicyclo[3.3.1]nonane-9-carboxylate | B 14 and 20 | AG | $^1$H NMR (400 MHz, Methanol-d4) δ 1.04-1.18 (m, 8H), 1.21-1.30 (m, 3H), 1.37-1.67 (m, 5H), 1.92-2.24 (m, 4H), 3.04-3.16 (m, 2H), 3.60-3.75 (m, 2H), 4.04-4.19 (m, 2H), 4.36-4.52 (m, 2H), 4.90-5.01 (m, 1H) Four protons obscured by solvent peaks | 1 E | m/z 368 (M + H)$^+$ (ES$^+$), at 3.93 min, 202 nm |
| 8-1 | Isomer 1: Ethyl 7-(3-((azepane-1-carbonyl)oxy)azetidin-1-yl)-3-oxa-9-azabicyclo[3.3.1]nonane-9-carboxylate | B 32 and 36 | AH | $^1$H NMR (400 MHz, Methanol-d4) δ 1.23-1.32 (m, 3H), 1.35-1.47 (m, 2H), 1.51-1.63 (m, 4H), 1.65-1.77 (m, 4H), 2.03-2.30 (m, 3H), 3.07-3.22 (m, 2H), 3.37-3.65 (m, 8H), 3.66-3.79 (m, 2H), 4.09-4.28 (m, 4H), 4.91-5.01 (m, 1H) | 4 B | m/z 396 (M +H)$^+$ (ES$^+$), at 4.68 min, 202 nm |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen*, 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After min, a 4 μL sample was transferred to 384-well plate and 7 μL of detection mixture added. Plates were incubated for 2 h with gentle agitation in the dark and then read on a PHERAstar plate reader. pEC$_{50}$ and E$_{max}$ figures were calculated from the resulting data for each receptor subtype and the results are set out in Table 4 below.

For the vast majority of examples at least two diastereomers exist and these have been separated, unless otherwise stated, using the techniques of reversed phase HPLC, chiral HPLC or chiral SFC. Isomer assignment (Isomer 1, Isomer 2, etc.) is based on the retention time of the compound using the separation technique that was performed in the final purification step. By implication, this could be reversed phase HPLC, chiral HPLC or chiral SFC retention time, and this will vary from compound to compound.

Analytical data for active isomers is reported in Table 3. Data for some weakly active compounds are included in Table 4 to highlight the preference for absolute stereochemistry.

NT=not tested

TABLE 4

| | Muscarinic Activity | | | |
|---|---|---|---|---|
| Ex. No. | pEC$_{50}$ M1 (% Emax cf. ACh) | pEC$_{50}$ M2 (% Emax cf. ACh) | pEC$_{50}$ M3 (% Emax cf. ACh) | pEC$_{50}$ M4 (% Emax cf. ACh) |
| ACh | 8.33 (102) | 7.82 (105) | 8.12 (115) | 8.09 (110) |
| 1-1 Isomer 2 | 6.50 (100) | 5.90 (58) | <4.70 (28) | 6.70 (85) |
| 1-2 Isomer mixture | 6.74 (100) | NT | NT | <4.70 (7) |
| 1-3 Isomer 2 | 6.94 (103) | NT | NT | <4.70 (19) |
| 1-4 Isomer mixture | 6.51 (84) | <4.70 (21) | <4.70 (6) | <4.70 (17) |
| 2-1 Isomer 1 | 6.68 (67) | <4.70 (13) | <4.70 (6) | <4.70 (9) |
| 2-2 Isomer 1 | 7.72 (95) | <4.70 (8) | <4.70 (12) | 6.59 (36) |
| 2-2 Isomer 2 | 6.64 (65) | <4.70 (6) | <4.70 (7) | <4.70 (31) |
| 2-3 Isomer 1 | 6.69 (88) | <4.70 (10) | <4.70 (9) | 5.19 (46) |
| 2-4 Isomer 1 | 5.99 (58) | NT | NT | <4.70 (9) |
| 2-5 Isomer 1 | 6.96 (64) | <4.70 (53) | <4.70 (35) | <4.70 (23) |
| 3-1 Isomer 1 | 6.09 (106) | NT | NT | <4.70 (23) |
| 3-2 Isomer 1 | 5.32 (68) | NT | NT | 6.03 (68) |
| 3-3 Isomer 1 | 6.50 (117) | <4.70 (5) | <4.70 (9) | 5.89 (55) |
| 4-1 | 6.08 (83) | NT | NT | 5.77 (57) |
| 4-2 Isomer 2 | 6.80 (105) | <4.70 (14) | <4.70 (17) | 6.55 (89) |
| 4-3 Isomer 2 | 6.43 (104) | NT | NT | 5.99 (46) |
| 4-4 Isomer 1 | 7.23 (67) | <4.70 (5) | <4.70 (0) | 7.64 (37) |
| 4-5 Isomer 1 | 7.80 (66) | <4.70 (6) | <4.70 (54) | 7.48 (31) |
| 4-5 Isomer 2 | 5.95 (44) | NT | NT | <4.70 (10) |
| 4-6 Isomer 1 | 6.20 (92) | NT | NT | 5.95 (33) |
| 4-6 Isomer 2 | 6.67 (93) | <4.70 (9) | <4.70 (11) | 6.47 (32) |
| 4-7 Isomer 1 | 7.12 (51) | <4.70 (7) | <4.70 (8) | 7.31 (29) |
| 4-8 Isomer 1 | 7.24 (72) | <4.70 (2) | <4.70 (4) | <4.70 (14) |

TABLE 4-continued

| Ex. No. | Muscarinic Activity | | | |
|---|---|---|---|---|
| | pEC$_{50}$ M1 (% Emax cf. ACh) | pEC$_{50}$ M2 (% Emax cf. ACh) | pEC$_{50}$ M3 (% Emax cf. ACh) | pEC$_{50}$ M4 (% Emax cf. ACh) |
| 4-9 Isomer 1 | 7.24 (37) | <4.70 (3) | <4.70 (2) | <4.70 (7) |
| 4-9 Isomer 2 | 5.25 (84) | NT | NT | 6.41 (85) |
| 5-1 Isomer mixture | 7.05 (83) | <4.70 (18) | <4.70 (45) | 6.37 (39) |
| 5-2 Isomer mixture | 5.65 (92) | NT | NT | <4.70 (19) |
| 6-1 Isomer 1 | 5.98 (65) | NT | NT | <4.70 (9) |
| 6-2 Isomer 1 | 5.16 (83) | NT | NT | 6.19 (55) |
| 6-3 Isomer 1 | 6.45 (92) | NT | NT | 5.79 (35) |
| 6-4 Isomer 1 | 6.93 (86) | <4.70 (9) | <4.70 (5) | 6.31 (50) |
| 6-5 Isomer 1 | 6.09 (58) | NT | NT | <4.70 (27) |
| 7-1 Isomer 1 | 5.89 (88) | NT | NT | 5.64 (29) |
| 8-1 Isomer 1 | 6.59 (104) | NT | NT | 5.73 (43) |

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

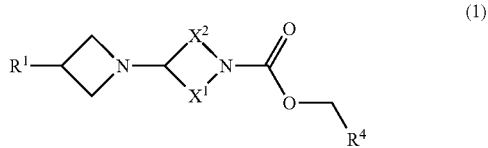

(1)

or a pharmaceutically acceptable salt thereof, wherein:

$X^1$ and $X^2$ are saturated hydrocarbon groups which together contain a total of five to nine carbon atoms and zero or one oxygen atoms and which link together such that the moiety:

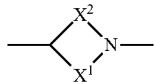

forms a monocyclic or bicyclic ring system optionally substituted with one or more fluorine atoms;

$R^1$ is selected from $COR^5$, $COOR^5$, $CONR^5R^6$, $C(=NR^5)R^6$, $OCOR^5$, $NR^7COR^5$, $NR^7CONR^5R^6$, $NR^7COOR^5$, $OCONR^5R^6$, $CH_2OR^5$, $CH_2NR^5R^6$, $CH_2COR^5$, $CH_2COOR^5$, $CH_2CONR^5R^6$, $CH_2C(=NR^5)R^6$, $CH_2OCOR^5$, $CH_2NR^7COR^5$, $CH_2NR^7CONR^5R^6$, $CH_2NR^7COOR^5$, $CH_2OCONR^5R^6$, $CH_2CH_2NR^5R^6$, an optionally substituted 5- or 6-membered ring containing 0, 1, 2, or 3 heteroatoms selected from O, N and S, and oxidized forms thereof, and a $C_{1-6}$ non-aromatic hydrocarbon group which is optionally substituted with one to six fluorine atoms, or which is optionally substituted with a 5- or 6-membered ring containing 0, 1, 2, or 3 heteroatoms selected from O, N and S, and oxidized forms thereof, wherein one or two, but not all, carbon atoms of the hydrocarbon group may optionally be replaced by a heteroatom selected from O, N and S, and oxidized forms thereof;

$R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S, and oxidized forms thereof; and $R^5$, $R^6$ and $R^7$ are each independently selected from hydrogen and a non-aromatic $C_{1-6}$ hydrocarbon group optionally substituted with one or more fluorine atoms or optionally substituted with a 5- or 6-membered ring containing 0, 1, 2, or 3 heteroatoms selected from O, N and S and oxidized forms thereof, or $R^5$ and $R^6$ are joined together to form an optionally substituted monocyclic or bicyclic ring containing 0, 1, 2, or 3 heteroatoms selected from O, N and S, and oxidized forms thereof.

2. The compound according to claim 1, or a pharmaceutically acceptable salt thereof, wherein $R^1$ is selected from $CH_2CONR^5R^6$, $OCONR^5R^6$, and a $C_{1-6}$ non-aromatic hydrocarbon group which is substituted with a 5- or 6-membered ring containing 0, 1, 2, or 3 heteroatoms selected from O, N and S and oxidized forms thereof.

3. The compound according to claim 1, or a pharmaceutically acceptable salt thereof, wherein $R^1$ is selected from $CH_2CONR^5R^6$ and $OCONR^5R^6$.

4. The compound according to claim 1, or a pharmaceutically acceptable salt thereof, wherein $R^5$ is selected from $C_1$-$C_3$ alkyl, or $R^5$ and $R^6$ are joined together to form a monocyclic or bicyclic ring containing 0, 1, 2, or 3 heteroatoms selected from O, N and S and oxidized forms thereof.

5. The compound according to claim 1, or a pharmaceutically acceptable salt thereof, wherein $R^6$ is selected from $C_1$-$C_3$ alkyl, or $R^6$ and $R^5$ are joined together to form a monocyclic or bicyclic ring containing 0, 1, 2, or 3 heteroatoms selected from O, N and S and oxidized forms thereof.

6. The compound according to claim 1, or a pharmaceutically acceptable salt thereof, wherein $R^5$ and $R^6$ are joined together to form a 4 to 7 membered ring containing 0 or 1 oxygen atoms.

7. The compound according to claim 1, or a pharmaceutically acceptable salt thereof, wherein $R^1$ is selected from:

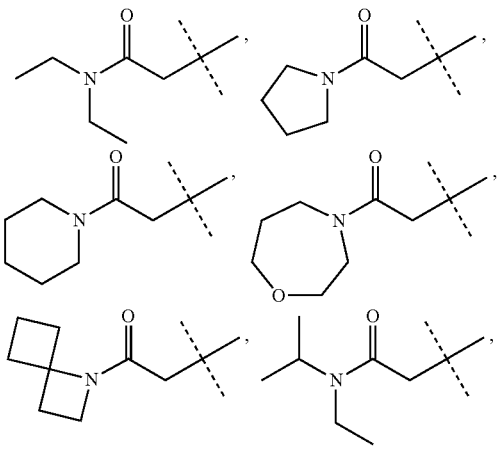

-continued

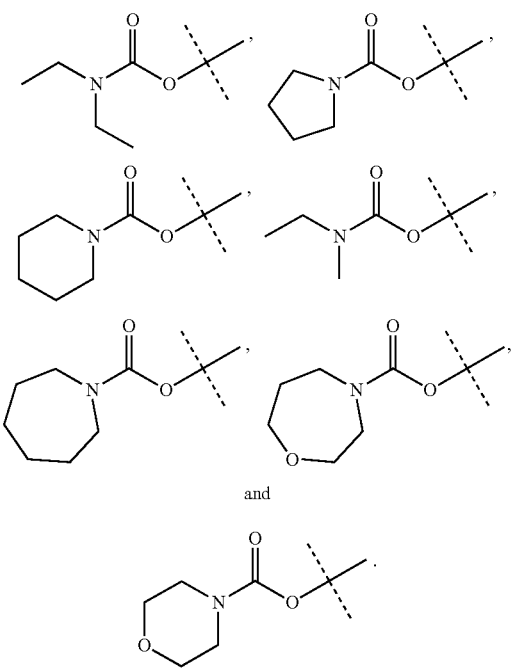

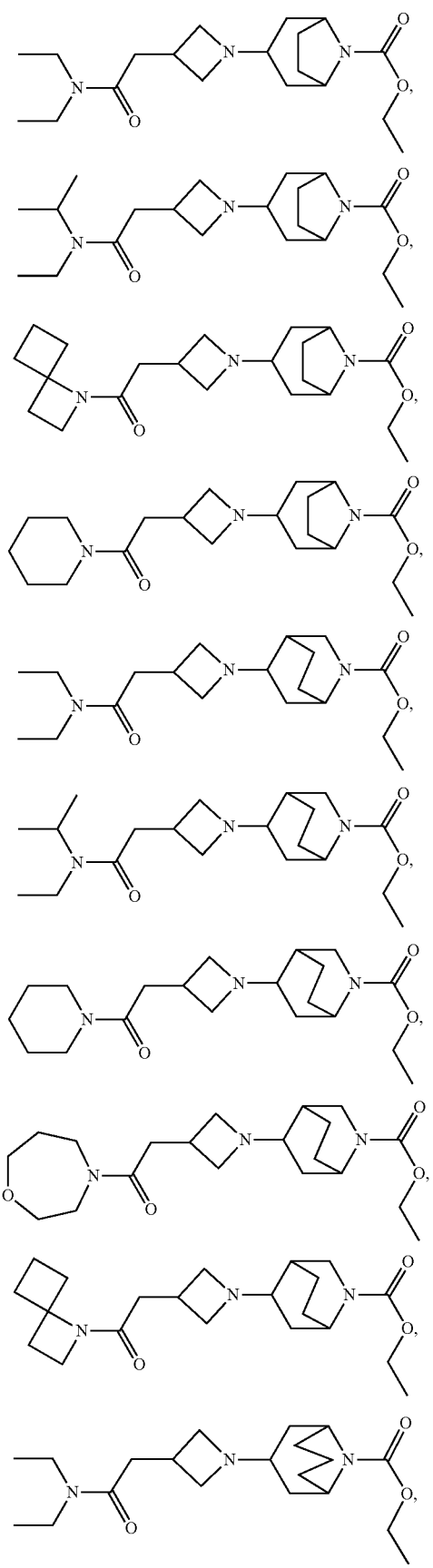

8. The compound according to claim 1, or a pharmaceutically acceptable salt thereof, wherein $R^4$ is selected from H, methyl, ethyl, ethynyl, and 1-propynyl.

9. The compound according to claim 1, or a pharmaceutically acceptable salt thereof, wherein the bicyclic ring system formed by the moiety:

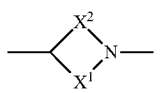

is selected from ring systems below:

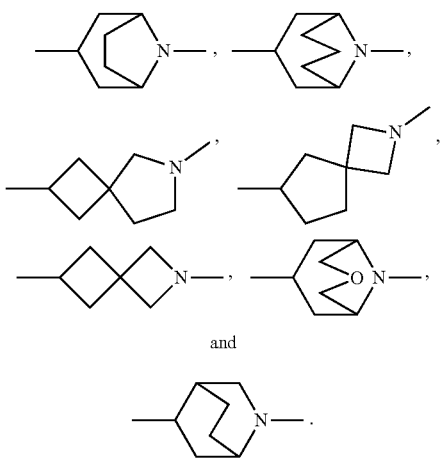

10. The compound according to claim 1, wherein the compound is selected from:

-continued
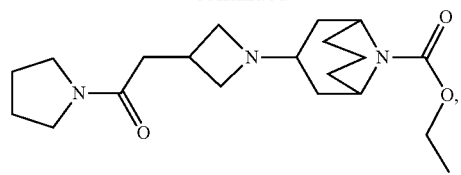
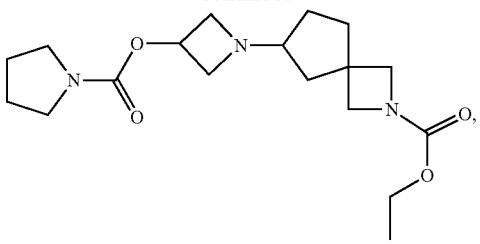

-continued

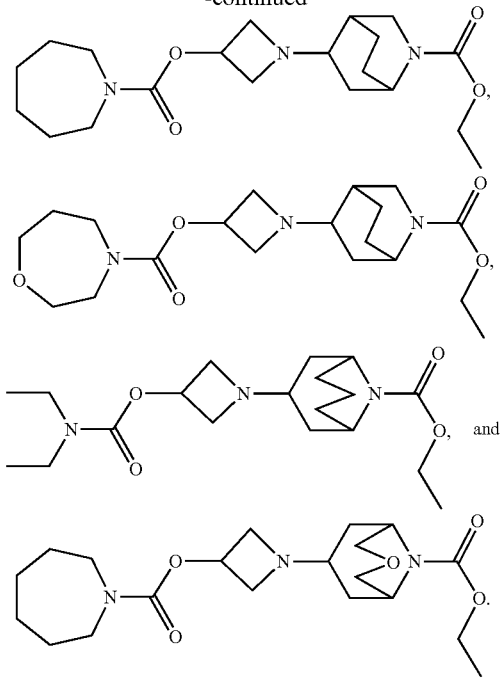

11. The compound according to claim 1, wherein the compound is selected from:
ethyl-3-(3-(2-(diethylamino)-2-oxoethyl)azetidin-1-yl)-8-azabicyclo[3.2.1]octane-8-carboxylate;
ethyl-3-(3-(2-(ethyl(isopropyl)amino)-2-oxoethyl)azetidin-1-yl)-8-azabicyclo[3.2.1]octane-8-carboxylate;
ethyl-3-(3-(2-oxo-2-(1-azaspiro[3.3]heptan-1-yl)ethyl)azetidin-1-yl)-8-azabicyclo[3.2.1]octane-8-carboxylate;
ethyl-3-(3-(2-oxo-2-(piperidin-1-yl)ethyl)azetidin-1-yl)-8-azabicyclo[3.2.1]octane-8-carboxylate;
ethyl-5-(3-(2-(diethylamino)-2-oxoethyl)azetidin-1-yl)-2-azabicyclo[2.2.2]octane-2-carboxylate;
ethyl-5-(3-(2-(ethyl(isopropyl)amino)-2-oxoethyl)azetidin-1-yl)-2-azabicyclo[2.2.2]octane-2-carboxylate;
ethyl-5-(3-(2-oxo-2-(piperidin-1-yl)ethyl)azetidin-1-yl)-2-azabicyclo[2.2.2]octane-2-carboxylate;
ethyl-5-(3-(2-(1,4-oxazepan-4-yl)-2-oxoethyl)azetidin-1-yl)-2-azabicyclo[2.2.2]octane-2-carboxylate;
ethyl-5-(3-(2-oxo-2-(1-azaspiro[3.3]heptan-1-yl)ethyl)azetidin-1-yl)-2-azabicyclo[2.2.2]octane-2-carboxylate;
ethyl-3-(3-(2-(diethylamino)-2-oxoethyl)azetidin-1-yl)-9-azabicyclo[3.3.1]nonane-9-carboxylate;
ethyl-3-(3-(2-oxo-2-(pyrrolidin-1-yl)ethyl)azetidin-1-yl)-9-azabicyclo[3.3.1]nonane-9-carboxylate;
ethyl-3-(3-(2-oxo-2-(piperidin-1-yl)ethyl)azetidin-1-yl)-9-azabicyclo[3.3.1]nonane-9-carboxylate;
ethyl 6-(3-(((diethylcarbamoyl)oxy)azetidin-1-yl)-2-azaspiro[3.3]heptane-2-carboxylate;
ethyl 2-(3-(((diethylcarbamoyl)oxy)azetidin-1-yl)-6-azaspiro[3.4]octane-6-carboxylate;
1-(6-(ethoxycarbonyl)-6-azaspiro[3.4]octan-2-yl)azetidin-3-yl 1,4-oxazepane-4-carboxylate;
ethyl 6-(3-(((ethyl(methyl)carbamoyl)oxy)azetidin-1-yl)-2-azaspiro[3.4]octane-2-carboxylate;
ethyl 6-(3-(((diethylcarbamoyl)oxy)azetidin-1-yl)-2-azaspiro[3.4]octane-2-carboxylate;
methyl 6-(3-(((diethylcarbamoyl)oxy)azetidin-1-yl)-2-azaspiro[3.4]octane-2-carboxylate;
ethyl 6-(3-(((pyrrolidine-1-carbonyl)oxy)azetidin-1-yl)-2-azaspiro[3.4]octane-2-carboxylate;
1-(2-(ethoxycarbonyl)-2-azaspiro[3.4]octan-6-yl)azetidin-3-yl morpholine-4-carboxylate;
1-(2-(ethoxycarbonyl)-2-azaspiro[3.4]octan-6-yl)azetidin-3-yl 1,4-oxazepane-4-carboxylate;
ethyl 3-(3-(((azepane-1-carbonyl)oxy)azetidin-1-yl)-8-azabicyclo[3.2.1]octane-8-carboxylate;
1-(8-(ethoxycarbonyl)-8-azabicyclo[3.2.1]octan-3-yl)azetidin-3-yl 1,4-oxazepane-4-carboxylate;
ethyl 5-(3-(((diethylcarbamoyl)oxy)azetidin-1-yl)-2-azabicyclo[2.2.2]octane-2-carboxylate;
ethyl 5-(3-(((pyrrolidine-1-carbonyl)oxy)azetidin-1-yl)-2-azabicyclo[2.2.2]octane-2-carboxylate;
ethyl 5-(3-(((piperidine-1-carbonyl)oxy)azetidin-1-yl)-2-azabicyclo[2.2.2]octane-2-carboxylate;
ethyl 5-(3-(((azepane-1-carbonyl)oxy)azetidin-1-yl)-2-azabicyclo[2.2.2]octane-2-carboxylate;
1-(2-(ethoxycarbonyl)-2-azabicyclo[2.2.2]octan-5-yl)azetidin-3-yl 1,4-oxazepane-4-carboxylate;
ethyl 3-(3-(((diethylcarbamoyl)oxy)azetidin-1-yl)-9-azabicyclo[3.3.1]nonane-9-carboxylate; and
ethyl 7-(3-(((azepane-1-carbonyl)oxy)azetidin-1-yl)-3-oxa-9-azabicyclo[3.3.1]nonane-9-carboxylate;
or a pharmaceutically acceptable salt thereof.

12. A pharmaceutical composition comprising a compound according to claim 1, or a pharmaceutically acceptable salt thereof, and a pharmaceutically acceptable excipient.

13. A method of lessening the severity of acute, chronic, neuropathic, or inflammatory pain in a subject, or treating a subject suffering from a disorder selected from Alzheimer's disease and dementia with Lewy bodies, comprising administering an effective amount of a compound according to claim 1, or a pharmaceutically acceptable salt thereof, to the subject in need thereof.

14. The method according to claim 13 wherein the disorder is Alzheimer's disease.

15. The method according to claim 13 wherein the disorder is dementia with Lewy bodies.

* * * * *